US008685957B1

(12) United States Patent
Lai et al.

(10) Patent No.: US 8,685,957 B1
(45) Date of Patent: Apr. 1, 2014

(54) TAZOBACTAM ARGININE COMPOSITIONS

(71) Applicants: Jan-Ji Lai, Westborough, MA (US); Jian-Qiao Gu, Lexington, MA (US); Pradip M. Pathare, Lexington, MA (US); Valdas Jurkauskas, Cambridge, MA (US); Joseph Terracciano, Concord, MA (US); Nicole Miller Damour, Belmost, MA (US)

(72) Inventors: Jan-Ji Lai, Westborough, MA (US); Jian-Qiao Gu, Lexington, MA (US); Pradip M. Pathare, Lexington, MA (US); Valdas Jurkauskas, Cambridge, MA (US); Joseph Terracciano, Concord, MA (US); Nicole Miller Damour, Belmost, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 13/828,534

(22) Filed: Mar. 14, 2013

Related U.S. Application Data

(63) Continuation of application No. 13/628,742, filed on Sep. 27, 2012, now Pat. No. 8,476,425.

(51) Int. Cl.
 *A61K 31/43* (2006.01)
 *C07D 499/00* (2006.01)

(52) U.S. Cl.
 USPC ........................................... 514/192; 540/304

(58) Field of Classification Search
 USPC .................... 540/304; 514/192, 195
 See application file for complete search history.

(56) References Cited

U.S. PATENT DOCUMENTS

| | | | |
|---|---|---|---|
| 4,200,575 A | 4/1980 | Numata et al. |
| 4,246,405 A | 1/1981 | Takaya et al. |
| 4,255,431 A | 3/1981 | Junggren et al. |
| 4,264,597 A | 4/1981 | Hashimoto et al. |
| 4,267,176 A | 5/1981 | Kamiya et al. |
| 4,268,509 A | 5/1981 | Teraji et al. |
| 4,284,631 A | 8/1981 | Takaya et al. |
| 4,291,031 A | 9/1981 | Takaya et al. |
| 4,298,529 A | 11/1981 | Ueda et al. |
| 4,299,829 A | 11/1981 | Kamiya et al. |
| 4,305,937 A | 12/1981 | Kamiya et al. |
| 4,327,093 A | 4/1982 | Ueda et al. |
| 4,331,665 A | 5/1982 | Teraji et al. |
| 4,332,798 A | 6/1982 | Teraji et al. |
| 4,332,800 A | 6/1982 | Teraji et al. |
| 4,336,253 A | 6/1982 | Lunn |
| 4,338,313 A | 7/1982 | Teraji et al. |
| 4,339,449 A | 7/1982 | Hashimoto et al. |
| 4,363,807 A | 12/1982 | Takaya et al. |
| 4,367,228 A | 1/1983 | Takaya et al. |
| 4,368,325 A | 1/1983 | Ueda et al. |
| 4,369,312 A | 1/1983 | Hashimoto et al. |
| 4,370,326 A | 1/1983 | Takaya et al. |
| 4,381,299 A | 4/1983 | Teraji et al. |
| 4,390,534 A | 6/1983 | Teraji et al. |
| 4,394,384 A | 7/1983 | Takaya et al. |
| 4,402,955 A | 9/1983 | Lunn |
| 4,405,617 A | 9/1983 | Takaya et al. |
| 4,407,798 A | 10/1983 | Kamiya et al. |
| 4,409,214 A | 10/1983 | Takaya et al. |
| 4,409,215 A | 10/1983 | Takaya et al. |
| 4,409,217 A | 10/1983 | Takaya et al. |
| 4,416,879 A | 11/1983 | Takaya et al. |
| 4,420,477 A | 12/1983 | Takaya et al. |
| 4,423,213 A | 12/1983 | Takaya et al. |
| 4,425,340 A | 1/1984 | Teraji et al. |
| 4,425,341 A | 1/1984 | Takaya et al. |
| 4,427,677 A | 1/1984 | Takaya et al. |
| 4,430,499 A | 2/1984 | Wheeler |
| 4,431,642 A | 2/1984 | Teraji et al. |
| 4,436,912 A | 3/1984 | Wheeler |
| 4,438,113 A | 3/1984 | Takaya et al. |
| 4,443,443 A | 4/1984 | Ueda et al. |
| 4,443,444 A | 4/1984 | Takaya et al. |
| 4,447,429 A | 5/1984 | Teraji et al. |
| 4,450,270 A | 5/1984 | Lunn |
| 4,452,851 A | 6/1984 | Takaya et al. |
| 4,457,928 A | 7/1984 | Teraji et al. |
| 4,462,999 A | 7/1984 | Takaya et al. |
| 4,463,000 A | 7/1984 | Teraji et al. |
| 4,463,002 A | 7/1984 | Takaya et al. |
| 4,463,003 A | 7/1984 | Takaya et al. |
| 4,464,369 A | 8/1984 | Takaya et al. |
| 4,470,980 A | 9/1984 | Higuchi et al. |
| 4,474,779 A | 10/1984 | Nagano et al. |
| 4,477,447 A | 10/1984 | Ueda et al. |
| 4,487,768 A | 12/1984 | Takaya et al. |
| 4,495,182 A | 1/1985 | Teraji et al. |
| 4,496,562 A | 1/1985 | Takaya et al. |

(Continued)

FOREIGN PATENT DOCUMENTS

| | | | |
|---|---|---|---|
| AU | 614793 B1 | 5/1989 |
| AU | 707730 B2 | 5/1996 |

(Continued)

OTHER PUBLICATIONS

Abstract for Moulds et al.,. Impact of characterized resistance mechanisms on the susceptibility of *Pseudomonas aeruginosa* to CXA-101. 50th Annual Interscience Conference on Antimicrobial Agents and Chemotherapy (ICAAC 2010); Sep. 12-15, 2010. Poster C1-1415; This poster is obtainable at: http://www.cubist.com/downloads/Moulds.PP.ICAAC_2010.Impact_of_resis_mech_on_suscep_of_P_aeruginosato_CXA_JNS.pdf.

(Continued)

*Primary Examiner* — Andrew D Kosar
*Assistant Examiner* — Laura Daniel
(74) *Attorney, Agent, or Firm* — Lathrop & Gage LLP; Brian C. Trinque

(57) ABSTRACT

This disclosure provides compositions containing solid forms of tazobactam arginine, and methods of manufacturing and using these compositions.

6 Claims, 10 Drawing Sheets

(56) References Cited

U.S. PATENT DOCUMENTS

| | | |
|---|---|---|
| 4,499,088 A | 2/1985 | Takaya et al. |
| 4,501,739 A | 2/1985 | Lunn et al. |
| 4,515,788 A | 5/1985 | Takaya et al. |
| 4,521,413 A | 6/1985 | Teraji et al. |
| 4,546,101 A | 10/1985 | Takaya et al. |
| 4,550,102 A | 10/1985 | Teraji et al. |
| 4,559,334 A | 12/1985 | Takaya et al. |
| 4,563,449 A | 1/1986 | Teraji et al. |
| 4,577,014 A | 3/1986 | Lunn et al. |
| 4,584,290 A | 4/1986 | Takaya et al. |
| 4,585,872 A | 4/1986 | Teraji et al. |
| 4,590,186 A | 5/1986 | Takaya et al. |
| 4,600,772 A | 7/1986 | O'Callaghan et al. |
| 4,608,373 A | 8/1986 | Shibanuma et al. |
| 4,609,730 A | 9/1986 | Takaya et al. |
| 4,622,318 A | 11/1986 | Takaya et al. |
| 4,626,384 A | 12/1986 | Tanaka et al. |
| 4,631,274 A | 12/1986 | Takaya et al. |
| 4,640,915 A | 2/1987 | Hashimoto et al. |
| 4,647,556 A | 3/1987 | Lattrell et al. |
| 4,667,028 A | 5/1987 | Schwab et al. |
| 4,690,921 A | 9/1987 | Shibanuma et al. |
| 4,692,443 A | 9/1987 | Katner |
| 4,698,337 A | 10/1987 | Takaya et al. |
| 4,699,980 A | 10/1987 | Shibanuma et al. |
| 4,703,046 A | 10/1987 | Ueda et al. |
| 4,705,851 A | 11/1987 | Takaya et al. |
| 4,735,937 A | 4/1988 | Heusler et al. |
| 4,748,172 A | 5/1988 | Katner |
| 4,761,410 A | 8/1988 | Takaya et al. |
| 4,764,606 A | 8/1988 | Imai et al. |
| 4,808,711 A | 2/1989 | Shimizu et al. |
| 4,822,787 A | 4/1989 | Murata et al. |
| 4,833,134 A | 5/1989 | Kishimoto et al. |
| 4,861,769 A | 8/1989 | Takaya et al. |
| 4,868,174 A | 9/1989 | Takaya et al. |
| 4,871,730 A | 10/1989 | Takaya et al. |
| 4,882,434 A | 11/1989 | Yoshioka |
| 4,921,852 A | 5/1990 | Murata et al. |
| 4,923,857 A | 5/1990 | Murata et al. |
| 4,927,818 A | 5/1990 | Takaya et al. |
| 4,935,507 A | 6/1990 | Takaya et al. |
| 4,943,567 A | 7/1990 | Nishizawa et al. |
| 4,952,578 A | 8/1990 | Sakane et al. |
| 4,960,766 A | 10/1990 | Takaya et al. |
| 4,963,543 A | 10/1990 | Murata et al. |
| 4,963,544 A | 10/1990 | Murata et al. |
| 4,971,962 A | 11/1990 | Oh et al. |
| 4,982,596 A | 1/1991 | Peterson et al. |
| 5,036,064 A | 7/1991 | Gotschi |
| RE33,778 E | 12/1991 | Iwanami et al. |
| 5,071,979 A | 12/1991 | Lattrell et al. |
| 5,073,550 A | 12/1991 | Gotschi |
| 5,081,116 A | 1/1992 | Nagano et al. |
| 5,095,012 A | 3/1992 | Okita et al. |
| 5,102,877 A | 4/1992 | Murata et al. |
| 5,104,866 A | 4/1992 | Sakane et al. |
| 5,108,997 A | 4/1992 | Takaya et al. |
| 5,109,130 A | 4/1992 | Sakane et al. |
| 5,138,066 A | 8/1992 | Gotschi |
| 5,159,070 A | 10/1992 | Heymes et al. |
| 5,162,520 A | 11/1992 | Takaya et al. |
| 5,173,485 A | 12/1992 | Sakane et al. |
| 5,179,485 A | 1/1993 | Tamayama |
| 5,187,160 A | 2/1993 | Sakane et al. |
| 5,210,080 A | 5/1993 | Takaya et al. |
| 5,215,982 A | 6/1993 | Sakane et al. |
| 5,215,983 A | 6/1993 | Murata et al. |
| 5,219,848 A | 6/1993 | Hennequin et al. |
| 5,234,920 A | 8/1993 | Okita et al. |
| 5,244,890 A | 9/1993 | Yamanaka et al. |
| 5,281,589 A | 1/1994 | Kim et al. |
| 5,286,721 A | 2/1994 | Murata et al. |
| 5,319,140 A | 6/1994 | Gotschi |
| 5,329,002 A | 7/1994 | Albrecht et al. |
| 5,336,768 A | 8/1994 | Albrecht et al. |
| 5,366,970 A | 11/1994 | Sakane et al. |
| 5,389,627 A | 2/1995 | Kim et al. |
| 5,498,787 A | 3/1996 | Wang et al. |
| 5,523,400 A | 6/1996 | Wei et al. |
| 5,637,580 A | 6/1997 | White et al. |
| 5,646,139 A | 7/1997 | White et al. |
| 5,648,346 A | 7/1997 | White et al. |
| 5,656,623 A | 8/1997 | White et al. |
| 5,661,144 A | 8/1997 | Tsushima et al. |
| 5,663,163 A | 9/1997 | Takaya et al. |
| 5,763,603 A | 6/1998 | Trickes |
| 6,214,818 B1 | 4/2001 | Nishitani et al. |
| 6,458,950 B1 | 10/2002 | Nishitani et al. |
| 6,518,263 B1 | 2/2003 | Nishitani et al. |
| 6,800,621 B2 | 10/2004 | Nishitani et al. |
| 6,878,686 B2 | 4/2005 | Marquess et al. |
| 6,974,797 B2 | 12/2005 | Fatheree et al. |
| 6,995,138 B2 | 2/2006 | Marquess et al. |
| 7,067,481 B2 | 6/2006 | Fatheree et al. |
| 7,067,482 B2 | 6/2006 | Fatheree et al. |
| 7,129,232 B2 | 10/2006 | Ohki et al. |
| 7,179,801 B2 | 2/2007 | Ohki et al. |
| 7,192,943 B2 | 3/2007 | Yamanaka et al. |
| 7,279,458 B2 | 10/2007 | Fatheree et al. |
| 7,332,471 B2 | 2/2008 | Fatheree et al. |
| 7,341,993 B2 | 3/2008 | Fatheree et al. |
| 7,384,928 B2 | 6/2008 | Nishitani et al. |
| 7,417,143 B2 | 8/2008 | Gnanaprakasam et al. |
| 7,553,962 B2 | 6/2009 | Fatheree et al. |
| 7,601,690 B2 | 10/2009 | Fatheree et al. |
| 7,612,037 B2 | 11/2009 | Fatheree et al. |
| 7,649,080 B2 | 1/2010 | Fatheree et al. |
| 7,655,621 B2 | 2/2010 | Fatheree et al. |
| 7,728,127 B2 | 6/2010 | Fatheree et al. |
| 8,476,425 B1 | 7/2013 | Lai et al. |
| 2002/0115650 A1 | 8/2002 | Glinka |
| 2003/0130173 A1 | 7/2003 | Fatheree et al. |
| 2006/0241017 A1 | 10/2006 | Chandran |
| 2006/0287244 A1 | 12/2006 | Chandran |
| 2007/0219191 A1 | 9/2007 | Nishitani et al. |
| 2009/0137460 A1 | 5/2009 | Marquess et al. |
| 2011/0136763 A1 | 6/2011 | Xia et al. |
| 2013/0065874 A1 | 3/2013 | Chandorkar et al. |

FOREIGN PATENT DOCUMENTS

| | | |
|---|---|---|
| CA | 1235689 A1 | 4/1988 |
| CA | 2140701 | 7/1995 |
| CN | 99100092.7 | 12/1999 |
| CN | 200810238479.7 | 5/2009 |
| CN | 201110061045.6 | 3/2010 |
| CN | 200910169647.6 | 4/2010 |
| CN | 201010557481.8 | 4/2011 |
| EP | 0047977 B1 | 9/1981 |
| EP | 0111934 A2 | 6/1984 |
| EP | 137440 A2 | 4/1985 |
| EP | 0137442 A2 | 4/1985 |
| EP | 84111744 | 4/1985 |
| EP | 84306866 | 4/1985 |
| EP | 0318767 A2 | 6/1989 |
| EP | 318767 A2 | 6/1989 |
| EP | 0664117 A1 | 7/1995 |
| EP | 0678095 | 10/1995 |
| EP | 711774 A1 | 5/1996 |
| EP | 0711774 A1 | 5/1996 |
| EP | 1134222 B1 | 4/2005 |
| EP | 1554287 | 7/2005 |
| EP | 1587497 | 10/2005 |
| EP | 1711178 | 10/2006 |
| EP | 1799209 | 6/2007 |
| EP | 1919449 | 5/2008 |
| EP | 1959933 | 8/2008 |
| EP | 2015755 | 1/2009 |
| EP | 2063869 | 6/2009 |
| EP | 2086570 | 8/2009 |
| EP | 2120880 | 11/2009 |
| EP | 2136844 | 12/2009 |
| EP | 2203177 | 7/2010 |

(56) References Cited

FOREIGN PATENT DOCUMENTS

| | | |
|---|---|---|
| EP | 2280713 | 9/2011 |
| EP | 1154770 | 11/2011 |
| EP | 2440523 | 4/2012 |
| JP | 62103092 A | 5/1987 |
| JP | 62158290 A | 7/1987 |
| JP | 63051388 A | 3/1988 |
| JP | 63051389 A | 3/1988 |
| JP | 2088582 A | 3/1990 |
| JP | 2117678 A | 5/1990 |
| JP | 4288086 A | 10/1992 |
| JP | 5222058 A | 8/1993 |
| JP | 6056848 A | 3/1994 |
| JP | 6128268 A | 5/1994 |
| JP | 2005162670 A | 6/2005 |
| WO | WO 99/28308 | 6/1999 |
| WO | WO 99/64049 | 12/1999 |
| WO | WO0004915 A1 | 2/2000 |
| WO | WO 03/078440 | 9/2003 |
| WO | WO 2004/048551 | 6/2004 |
| WO | WO 2005/005436 | 1/2005 |
| WO | WO 2009/049086 | 4/2009 |
| WO | WO 2009/105782 | 8/2009 |
| WO | WO2013036783 A2 | 3/2013 |

OTHER PUBLICATIONS

Abstract for Umeh et al., A double-blind, randomized, phase 2 study to compare the safety and efficacy of intravenous CXA-101 and intravenous ceftazidime in complicated urinary tract infection. 50th Annual Interscience Conference on Antimicrobial Agents and Chemotherapy (ICAAC 2010); Sep. 12-15, 2010. Poster L1-361A; This poster is obtainable at: http://www.cubist.com/downloads/Umeh__ICAAC2010_08144v2.pdf.
Abstract for Brown et al. Activity profile of CXA-101 and CXA-101/ tazobactam against target gram-positive and gram-negative pathogens. 49th Annual Interscience Conference on Antimicrobial Agents and Chemotherapy (ICAAC 2009); Sep. 12-15, 2009. Poster F1-1986; This poster is obtainable at: http://www.eurofins.com/media/767069/Final%20F1-1986.pdf.
Abstract for Brown et al., Disk diffusion testing of CXA-101 and CXA-101 in combination with tazobactam against target pathogens. 49th Annual Interscience Conference on Antimicrobial Agents and Chemotherapy (ICAAC 2009); Sep. 12-15, 2009. Poster F1-1998; This poster is obtainable at: http://www.eurofins.com/media/767072/Final%20F1-1998.pdf.
Abstract for Brown et al., Quality control parameters for CXA-101 broth microdilution susceptibility tests. 49th Annual Interscience Conference on Antimicrobial Agents and Chemotherapy (ICAAC 2009); Sep. 12-15, 2009, Foster F1-1997.
Abstract for Craig et al., In vivo activity of CXA-101 plus a 2:1, 4:1, or 8:1 ratio of tazobactam against various Enterbacteriacae producing Extended-spectrum beta-lactamases in the thighs of neutropenic mice. 49th Annual Interscience Conferenc on Antimicrobial Agents and Chemotherapy (ICAAC 2009); Sep. 12-15, 2009. Poster F1-1999.
Abstract for Craig et al., In vivo activity of CXA-101, a new cephalosporin, against *Pseudomonas aeruginosa* and other Enterobacteriaceae in the thighs of neutrienic mice. 49th Annual Interscience Conference on Antimicrobial Agents and Chemotherapy (ICAAC 2009); Sep. 12-15, 2009. Poster F1-2002.
Abstract for Ge et al., CXA-101 population PK analysis and Monte Carlo simulation for PK/PD target attainment and dose regimen selection. 49th Annual Interscience Conference on Antimicrobial Agents and Chemothreapy (ICAAC 2009); Sep. 12-15, 2009. Poster F1-2003.
Abstract for Ge et al., PK study of CXA-101 in combination with tazobactam in dogs after intravenous administration 49th Annual Interscience Conference on Antimicrobial Agents and Chemotherapy (ICAAC 2009); Sep. 12-15, 2009. Poster F1-2001.

Abstract for Ge et al., PK and safety of CXA-101, a new antipseudomonal cephalosporin, in healthy adult subjects after single intravenous dosing. 49th Annual Interscience Conference on Antimicrobial Agents and Chemotherapy (ICAAC 2009); Sep. 12-15, 2009. Poster F1-2004.
Abstract for Giske et al., CXA-101 has high activity against clinical isolates of *Pseudomonas aeruginosa* including ceftazidime-resistant isolates. 49th Annual Interscience Conference on Antimicrobial Agents and Chemotherapy (ICAAC 2009); Sep. 12-15, 2009. Poster F1-1988.
Abstract for Jacqueline at al. FIC Index determination of CXA-101/ tazobactam in combination with amikacin, aztreonam, meropenem, levofloxacin, and tigecycline against *Escherichia coli, Klebsiella pneumoniae*, and *Pseudomonas aeruginosa* strains. 49th Annual Interscience Conference on Antimicrobial Agents and Chemotherapy (ICAAC 2009); Sep. 12-15, 2009. Poster F1-1995.
Abstract for Jacqueline et al. In vitro assessment using time-kill curves of CXA-101/tazobactam against *Eschericha coli, Klebsiella pneumoniae*, and *Pseudomonas aeruginosa* strains. 49th Annual Interscience Conference on Antimicrobial Agents and Chemotherapy (ICAAC 2009); Sep. 12-15, 2009. Poster F1-1996.
Abstract for Jacqueline et al. 50% effective dose determination of CXA-101 alone or in combination with tazobactam for treating experimental peritonitis in mice due to extended-spectrum beta-lactamase-producing *Escherichia coli* strains: comparison with ceftazidime and piperacillin/tazobactam. 49th Annual Interscience Conference on Antimicrobial Agents and Chemotherapy (ICAAC 2009); Sep. 12-15, 2009. Poster F1-2000.
Absract for Juan et al., Oliver A. Activity of the new cephalosporin CXA-101 against carbapenem-resistant *Pseudomonas aeruginosa* isolated form a Spanish multicenter study. 49th Annual Interscience Conference on Antimicrobial Agents and Chemotherapy (ICAAC 2009); Sep. 12-15, 2009. Psoster F1-1987.
Abstract for Moya et al. Affinity of the new cephalosporin CXA-101 to penicillin-binding proteins of *Pseudomonas aeruginosa*. 49th Annual Interscience Conference on Antimicrobial Agents and Chemotherapy (ICAAC 2009); Sep. 12-15, 2009. Poster F1-1985.
Abstract for Riera et al. Activity of the new cephalosporin CXA-101 against biofilms of relevant *P. aeruginosa* phenotypes in cystic fibrosis chronic respiratory infection: mucoid and hypermutable strains. 49th Annual Interscience Conference on Antimicrobial Agents and Chemotherapy (ICAAC 2009); Sep. 12-15, 2009. Poster F1-1990.
Abstract for Sader et al., Activity of the novel cephalosporin CXA-101 tested in combination with tazobactam against cephalosporin-resistnat Enterobacteriaceae, *P. aeruginosa* and *B. fragilis*. 49th Annual Interscience Conference on Antimicrobial Agents and Chemotherapy (ICAAC 2009): Sep. 12-15, 2009. Popster F1-1992; The poster is obtainable at: http:www.jmilabs.com/data/posters/ICAAC2009/F1-1992.pdf.
Abstract for Titelman et al. Activity of CXA-101 plus tazobactam against ESBL-producing *E. coli* and *K. pneumoniae*. 49th Annual Interscience Conference on Antimicrobial Agents and Chemotherapy (ICAAC 2009); Sep. 12-15, 2009. Poster F1-1993.
Abstract for Zamorano et al. Activity of the new cephalosporin CXA-101 against *P. aeruginosa* isolates from chronically infected cyctic fibrosis patients. 49th Annucla Interscience Conference on Antimicrobial Agents and Chemotherapy (ICAAC 2009); Sep. 12-15, 2009. Poster F1-1991.
Abstract for Brown et al. Activity profile of CXA-101 against gram-positive and gram-negative pathogens by broth and agar dilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-354; This poster is obtainable at: http://www.eurofins.com/media/694466/Calixa%20F1-354%20broth%20agar%20v6.pdf.
Abstract for Brown et al. Effect of various testing parameters on the activity of CXA-101 by broth microdilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-357; This poster is obtainable at: http://www.eurofins.com/media/694469/CAX%F1-357%20parameter%20v6.pdf.

(56) References Cited

OTHER PUBLICATIONS

Abstract for Brown et al. Mode of action of CXA-101 based on minimum bactericidal concentration analysis and time-kill kinetic analysis. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-358; This poster is obtainable at: http://www.eurofins.com/media/694472/CXA%20F1-358%th%20mbc%20v5.pdf.

Abstract for Livermore et al., Warner M. Activity of cephalosporin CXA-101 vs. *P. aeruginosa*. 48th Annual Interscience Conference on Antimicrobial Agents and Chemotherapy & the Infectioys Disease Society of America 46th Annual Meeting (ICAAC/ISDA 2008); Oct. 25-28, 2008. Poster F1-355; This poster is obtainable at: http://www.hpa.org.uk/webc/HPAwebFile/HPAweb_C/125354148015.

Abstract for Mushtaq et al. Activity of cephalosporin CXA-101 with B-lactamase inhibitors vs. Enterbacteriaceae. 48th Annual Interscience Conference on Antimicrobial Agents and Chemotherapy & the Infectious Diease Society of America 46th Annual Meeting (ICAAC/IDSA 2008); Oct. 25-28, 2008. Poster F1-356; This poster is obtainable at: http://www.hpa.org.uk/webc/HPAwebFile/HPAweb_C/1225354148047.

Abstract for Sader et al., Activity of the Novel Antimicrobial Ceftolozane/Tazobactam Tested Against Bacterial Isolated in USA Hopsitals from Patients with Pneumonia (2011). IDWeek 2012: A Joint Meeting of IDSA, SHEA, HIVMA, and PIDS; Oct. 17-21, 2012. Poster 846; This poster is obtainable at: http://www.jmilabs.com/data/posters/IDWeek2012/846.pdf.

Abstract for Walkty et al. In Vitro Activity of Ceftolozane/Tazobactam (CXA-201) versus *Pseudomonas aeruginosa* Isolates Obtained from Patients in Canadian Hospitals: CANWARD 2011. IDWeek 2012: A Joint Meeting of IDSA, SHEA, HIVMA, and PIDS; Oct. 17-21, 2012. Poster 1616; This poster is obtainable at: http://idsa.confex.com/idsa/2012/webprogram/Handout/id509/POSTER202_1616.pdf.

Abstract for Miller et al., Safety and Pharmacokinetics of Intravenour Ceftolozane/tazobactam 3 g every 8 Hours and Cumulative Fraction of Response in Plasma and Epithelial Lining Fluid in a Simulated Ventialtor Associated Pneumonia Population. 52nd Annual Interscience Conference on Antimicrobia Agents and Chemotherapy (ICAAC 2012); Sep. 9-12, 2012. Poster A-641.

Abstract for Sader et al., Activity of the Novel Antimicrobial Ceftolozane/Tazobactam Tested Against Contemporaty Clinical Strains form USA Hospitals (2011). 52nd Annual Interscience Conference on Antimicrobial Agents and Chemotherapy (ICAAC 2012); Sep. 9-12, 2012. Poster E-199.

Abstract for Soon et al., In vitro Pharmacodynamics of CXA-2001 (Ceftolozane/Tazobactam) against β-lactamase Producting *Echericia coli*. 52nd Annual Interscience Conference on Antimicrobial Agents and Chemotherapy (ICAAC 2012); Sep. 9-12, 2012. Poster E-201.

Abstract for Zhanel et al., In vitro Activity of Ceftolozane/tazobactam Tested Against 1,705 Gram-Negative Pathogens Isolated from Patients in Canadian Hospitals in 2011: CANWARD Surveillance Study. 52nd Annual Interscience Conference on Antimicrobial Agents and Chemotherapy (ICAAC 2012); Sep. 9-12, 2012. Poster E-200.

Abstract for Chandorkar et al. Intrapulmonary penetration of CXA-201 and Piperacillin/tazobactam in healthy adult subjects. 22nd Annual Meeting of the European Congress of Clinical Microbiology (ECCMID 2012); Mar. 21-Apr. 3, 2012. Poster P1627.

Abstract for Sader et al., Activity of the Novel Antimicrobial CXA-201 Tested Against Contemporary Clinical Strains from European Hospitals. 22nd Annual Meeting of the European Congress of Clinical Microbiology (ECCMID 2012); Mar. 31-Apr. 3, 2012. Poster P1446.

Abstract for Snydman et al., Activity of Ceftolozane/Tazobactam CXA-201 against 270 recent isolated from the bacteriodes group. 22nd Annual Meetings of the European Congress of Clinical Microbiology (ECCMID 2012); Mar. 31-Apr. 3, 2012. Poster; This poster is obtainable at: http://www.escmid.org/escmid_library/online_lecture_library/?search=1&current_page=1&search_term=snydman.

Abstract for Chandorkar et al. Intrapulmonary penetration of CXA-201 and Piperacillin/tazobactam in healthy adult subjects. 49th Annual Meeting of the Infectious Diseases Society of America (IDSA 2011); Oct. 20-23, 2011. Poster 611.

Abstract for Miller et al. Probability of Target Attainment of CXA-201 in Paients with Renal Hyperclearance. 49th Annual Meeting of the Infectious Diseases Society of America (ISDA 2011); Oct. 20-23, 2011. Poster B1-589.

Abstract for Killian et al. An Equivalency Study of a Sensititre Dried MIC Plate Compared with the CLSI Broth Microdilution Reference Method for CXA-201 and Comparator Antimicrobials. 51st Annual Interscience Conference on Antimicrobial Agents and Chemotherapy (ICAAC 2011); Sep. 17-20, 2011. Poster D-691A.

Abstract for Moya et al. Pan-β-lactam resistance development in *P. aeruginosa* clinical strains: molecular mechanisms, PBPs profiles and binding affinities. 51st Annual Interscience Conference on Antimicrobial Agents and Chemotherapy (ICAAC 2011); Sep. 17-20, 2011. Poster C1-619.

Abstract for Hershberger et al. CXA-101/Tazobactam Probability of Target Attainment using Population Pharmacokinetic Analysis. Joint Meeting of the European Congress of Clinical Microbiology and Infectious Diesases and International Congress of Chemotherapy (ECCMID-ICC 2011); May 7-12, 2011. Poster 1520; This poster is obtainable at: http://www.poster-submission.com/search/sresult.

Abstract for Miller et al. Pharmacokinetics of CXA-101/tazobactam in Subjects with mild or Moderate Renal Impairment. Joint Meeting of the European Congress fo Clinical Microbiology and Infectious Diseases and International Congress of Chemotherapy (ECCMID-ICC 2011); May 7-12, 2011. Poster 1519; This poster is obtainable at: http://www.poster-submission.com.

Abstract for Fenneteau et al. Population PK/PD Modeling and Simulations of a Fixed-Dose Combination of CXA-101 and Tazobactam to Optimize Dosing Strategies in Renally Impaired Patients with Complicatied Urinary Tract Infection. 3rd Biennial American Conference on Pharacometrics (ACoP 2011); Apr. 3-6, 2011; This poster is obtainable at: http://www.go-acop.org/sites/default/files/webform/posters/ACOP2011%20-%Dosing%20Strategies%20of%20CXA-101%20and%20Taz%20in%20cUTI%20Patients.pdf.

Abstract for Marier et al. Population PK Analysis of Intravenous CXA-101 in Subjects with Complicated Urinary Tract Infection, Including Pyelonephritis. 112th Annual Meeting of the American Society for Clinical Pharmacology and Therapeutics (ASCPT 2011); Mar. 2-5, 2011. Poster PII-49.

Abstract for Bulik et al. In vivo Efficacy of Human Simulated CXA-101 ± Tazobactam versus Pperacillin-Tazobactam against Phenotypically Diverse Gram-negative Organisms. ICAAC 2010. Poster A1-1381; This poster is obtainable at: http://www.cubist.com/downloads/Bulik_PP_ICAAC_2010_in_vivo_CXA-101_vs_TZP_against_gram_neg.pdf.

Abstract for Cabot et al. Activity of CXA-101 Against a Large Collection of *P. aeruginosa* Blood Stream Isolated Overexpressing AmpC and the Major Efflux Pumps. 50th Annual Interscience Conference on Antimicrobial Agents and Chemotherapy (ICAAC 2010); Sep. 12-15, 2010. Poster E-816.

Abstract for Jacqueline . Assessment of the In vivo Activity of CXA-101 in a Murine Model of *Pseudomonas aeruginosa* Pneumonia: Comparison with Ceftazidime and Piperacillin-Tazobactam. 50th Annual Interscience Conference on Antimicrobial Agents and Chemothreapy (ICAAC 2010); Sep. 12-15, 2010. Poster B-1401.

Abstract for Marier et al. Pharmacokinetics of a novel antipseudomonal cephalosporin, CXA-101, and tazobactam in healthy adult subjects. 50th Annual Interscience Conference on Antimicrobial Agents and Chemotherapy (ICAAC 2010); Sep. 12-15, 2010. Poster A1-1391.

International Conference on Harmonisation. Guideline for Good Clinical Practice. http://www.ich.org/products/guidelines/efficacy/efficacy-single/article/good-clinical-practice.html (Apr. 23, 2012, date last accessed), 53 pages.

(56) References Cited

OTHER PUBLICATIONS

Rodvold, et al: Penetration of anti-infective agents into pulmonary epithelial lining fluid: focus on antibacterial agents; Clin Pharmacokinet, 2011; vol. 50: pp. 637-664.

Bulik et al., In vitro activity of CXA-101, a novel cephalosporin, against resistant phenotypes of *Pseudomonas aeruginosa*. 47th Annual Meeting of the Infectious Diseases Society (IDSA 2009); Oct. 29-Nov. 1, 2009. Poster 209.

Livermore et al. Chequerboard titrations of cephalosporin CXA-101 and tazobactam vs. beta-lactamase producing Enterobacteriaceae. 49th Annual Interscience Conference on Antimicrobial Agents and Chemotherapy (ICAAC 2009); Sep. 12-15, 2009. Poster F1-1994.

Moya et al. Activity of CXA-101 against *Pseudomonas aeruginosa* beta-lactam resistance mechanisms: ampD, ampDh2, ampDh2, dacB, and oprD mutations. 49th Annual Interscience Conference on Antimicrobial Agents and Chemotherapy (ICAAC 2009); Sep. 12-15, 2009. Poster F1-1989.

Soon et al. A Novel Mathematical Modeling Approach to Characterize the Pharmacodynamics of Ceftolozane/Tazobactam, a β-lactam & β-lactamase Inhibitor Combination. 52nd Annual Interscience Conference on Antimicrobial Agents and Chemotherapy (ICAAC 2012); Sep. 9-12, 2012. Oral Presentation A•1762.

Miller et al. CXA-201 dose selection based on probability of target attainment and drug exposure in subjects with varying degrees of renal impairment. ICAAC 2011. Oral Presentation A-1099.

Steenbergen et al. Potency of CXA-101Tazobactam for Pathogens from ICU and non-ICU Correlated to Probability of Pharmacokinetic/ Pharmacodynamic (PK/PD) Target Attainment. ICAAC 2011. Oral Presentation A-1689.

Hatano et al. In vivo Anti-*Pseudomonas aeruginosa* Activity of Novel Parenteral Cephalosporin, FR264205. 45th Annual Interscience Conference on Antimicrobial Agents and Chemotherapy (ICAAC 2005); Dec. 16-19, 2005. Oral Presentation F-1165.

Strayer et al. Pharmacodynamics of Piperacillin Alone and in Combination with Tazobactam against Piperacillin-Resistant and -Susceptible Organisms in an In Vitro Model of Infection. Antimicrobial Agents and Chemotherapy 1994;38:2351.

Bush et al. Kinetic Interactions of Tazobactam with Beta-Lactamases from All Major Structural Classes. Antimicrobial Agents and Chemotherapy 1993;37:851.

Kurpiel. Point Mutations in the Inc Antisense RNA Gene Are Associated with Increased Plasmid Copy Number, Expression of BlaCMY-2 and Resistance to Piperacillin/Tazobactam in *Escherichia coli*. Journal of Antimicrobial Chemotherapy 2012;67:339.

Lister et al. Importance of Beta-Lactamase Inhibitor Pharmacokinetics in the Pharmacodynamics of Inhibitor-Drug Combinations: Studies with Piperacillin-Tazobactam and Piperacillin-sulbactam. Antimicrobial Agents and Chemotherapy 1997;41:721.

Thomson et al. Beta-Lactamase Production in Memebers of the Family Enterobacteriaceae and Resistance to Beta-Lactam-Enzyme Inhibitor Combinations. Antimicrobial Agents and Chemotherapy 1990;34:622.

Seetulsingh et al. Activity of Clavulanate Combinations against TEM-1 b-Lactamase-Producing *Escherichia coli* Isolates Obtained in 1982 and 1989. Journal fo Antimicrobial Chemotherapy 1991;27:749.

Alexov et al. Efficacy of Ampicillin-Sulbactam is not Dependent upon Maintenance of a Critical Ration between Components: Sulbactam Pharmacokinetics in Pharmacodynamic Interactions. Antimicrobial Agents Chemotherapy 1996;40:2468.

Louis et al., Pharmacodynamics of b-Lactamase Inhibition by NXL104 in Combination with Cefaroline: Examining Organisms with Multiple Types of b-Lacramases. Antimicrobial. Antimicrobial Agents and Chemotherapy. 2012, 56, 258.

Bulik et al, In vivo comparison of CXA-101 with and without tazobactam versus piperacillin-tazobactam using human simulated exposures against phenotypically diverse gram-negative organisms. Antimicrob Agent Chemother 2012 56 (1):544-9.

European Committee on Antimicrob Sus Testing 2012.

Ge et al., Pharmacokinetics and safety of CXA-101, a new antipseudomonal cephalosporin, in healthy adult male and female subjects receiving single- and multiple-dose intravenous infusions. Antimicrob Agents Chemother. 2010 ; 54 3427-31.

Juan et al., Activity of a new antipseudomonal cephalosporin, CXA-101, against carbapenem-resistant and multidrug-resistant *Pseudomonas aeruginosa* clinical strains. Antimicrob Agents Chemother. 2010:54(2):846-51.

Sader et al., Antimicrobial activity of CXA-101, a novel cephalosporin tested in combination with tazobactam against Enterobacteriaceae, *Pseudomonas aeruginosa*, and *Bacteroides fragilis* strains having various resistance phenotypes. Antimicrob Agents Chemother. 2011 55(5):2390-4.

Titelman et al., In vitro activity of CXA-101 plus tazobactam against CTX-M-14- and CTX-M-15-producing *Escherichia coli* and *Klebsiella pneumoniae*. Diagn Microbiol Infect Dis. 2011 70(1):137-41.

Jacqueline et al., Efficacy of ceftolozane in a murine model of *Pseudomonas aeruginosa* acute pneumonia: in vivo antimicrobial activity and impact on host inflammatory response. J Antimicrob Chemother. 2012, dks 343.

Moya et al., Pan-β-Lactam Resistance Development in *Pseudomonas aeruginosa* Clinical Strains: Molecular Mechanisms, Penicillin-Binding Protein Profiles, and Binding Affinities. Antimicrob Agents Chemother. 2012 56 4771-8.

Chandorkar et al., Intrapulmonary pentration of ceftolozane/tazobactam and piperacillin/tazobactam in healthy adult subjects. J Antimicrob Chemother. 2012, 67, 2463.

Miller et al., Pharmacokinetics and Safety of Intravenous Ceftolozane/tazobactam in Healthy Adult Subjects following Single and Multiple Ascending Doses. Antimicrob Agents Chemother. 2012 56:3086-91.

Moya et al., Affinity of the New Cephalosporin CXA-101 to Penicillin-Binding Proteins of *Pseudomonas aerginosa*. Antimicrob Agents Chemother. 2010; 54: 3933-3937.

Livermore et al., Chequerboard titration of cephalosporin CXA-101 and tazobactam versus beta-lactamase-producing Enterobacteriaceae. J Antimicrob Chemother. 2010 65 1972-4.

Zamorano et al., Activity of the new cephalosporin CXA-101 against *Pseudomonas aeruginosa* isolates from chronically-infected cystic fibrosis patients. Clin Microbiol Infect. 2010 16(9):1482-7.

Riera et al., Anti-biofilm and resistance suppression activities of CXA-101 against chronic respiratory infection phenotypes of *Pseudomonas aeruginosa* strain PAO1. J Antimicrob Chemother. 2010;65(7):1399-404.

Moya et al., Activity of a new Cephalosporin, CXA-101 (FR264205), against beta-lactam-resistant *Pseudomonas aeruginosa* mutants selected in vitro and after antipseudomonal treatment of intensive care unit patients. Antimicrob Agents Chemother. 2010 ;54(3):1213-7.

Bulik et al., In vitro potency of CXA-101, a novel cephalosporin, against *Pseudomonas aeruginosa* displaying various resistance phenotypes, including multidrug resistance. Antimicrob Agents Chemother. 2010;54(1):557-9.

Perletti et al., CXA-101—Cephalosporin Antibiotic. Drugs of the Future 2010; 35(12):977-986.

Livermore et al., Activity of cephalosporin CXA-101 against *Pseudomonas aeruginosa* and *Burkholderia cepacia* group strains and isolates. Int J Antimicrob Agents. 2009 ;34(5):402-6.

Giske et al., Activity of cephalosporin CXA-101 and comparators against extended-spectrum-{beta}-lactmase-producing *Pseudomonas aeruginosa*. J Antimicrob Chemother. 2009 ;64(2):430-1.

Toda et al., Synthesis and SAR of novel parenteral anti-pseudomonal cephalosporins: discovery of FR264205. Bioorg Med Chem Lett. 2008 ;18(17):4849-52.

Takeda et al., Stability of FR264205 against AmpC beta-lactamase of *Pseudomonas aeruginosa*. Int J Antimicrob Agents. Nov. 2007;30(5):443-5.

Takeda et al., In vitro and in vivo activities of a new cephalosporin, FR264205, against *Pseudomonas aeruginosa*. Antimicrob Agents Chemother. 2007 ;51(3):826-30.

(56) References Cited

OTHER PUBLICATIONS

Jacqueline. In vivo Activity of CXA-101 against *Pseudomonas aeruginosa* in Rabbit Experimental Pneumonia: Comparison with Ceftazidime Piperacillin-Tazobactam and Imipenem. 51st Annual Interscience Conference on Antimicrobial Agents and Chemotherapy (ICAAC 2011); Sep. 17-20, 2011, Poster B-590.
Reynolds et al., Enterbacteriaceae in the UK and Ireland: Susceptibility to Old and New Agents. 52nd Annual Interscience Conference on Antimicrobial Agents and Chemotherapy (ICAAC 2012); Sep. 9-12, 2012. Poster C2-152.
Cabot et al. Dynamics and mechanisms of resistance development to ceftazidime, meropenem and ceftolozane-/tazobactam in wild-type and mutator *P. aeruginosa* strains. 52nd Annual Interscience Conference on Antimicrobial Agents and Chemotherapy (ICAAC 2012); Sep. 9-12, 2012. Poster C1-1970.
Melchers et al., In vitro Activity of CXA-101 Alone and in Combination With Tazobactam Against Extended Spectrum Beta-lactamase Harbouring Enterobacteriaceae. 52nd Annual Interscience Conference on Antimicrobial Agents and Chemotherpy (ICAAC 2012); Sep. 9-12, 2012. Poster F1-2008.
Ambrose, et al: Pharmacokinetic-pharmacodynamic considerations in the design of hospital-acquired or ventilator associated bacterial pneumonia studies: look before you leap!; Clin Infect Dis, 2010, vol. 51, Suppl 1, pp. 5103-5110.
American Thoracic Society; Infectuous Diseases Society of America; Guidelines for the management of adults with hospital-acquired, ventilator-associated, and healthcare-associated pneumonia; Am J Respis Crit Care Med., 2005, vol. 171(4), pp. 388-416.
Baughman, et al: The disgnosis and treatment challenges in nosocomial pneumonia; Diagn Microbiol Infect Dis, 1999, vol. 33(2), pp. 131-139.
Bergogne-Berezin: Predicting the efficacy of antimicrobial agents in respiratory infections: is tissue concentration a valid measure?; J Antimicrob Chemother, 1995, vol. 35, pp. 363-371.
Boselli, et al: Steady-state plasma and intrapulmonary concentrations of piperacillin/tazobactam 4 g/0.5 g administered to critically ill patients with severe nosocomial pneumonia; Intensive Care Med, 2004, vol. 30, pp. 976-979.
Boselli, et al: Alveolar concentrations of piperacillin/tazobactam administered in continuous infusion to patients with ventilator-associated pneumonia; Crit Care Med, 2008, vol. 36, pp. 1500-1506.
Chastre, et al: Ventilator-associated pneumonia; Am J Respir Crit Care Med, 2002, vol. 165(7), pp. 867-903.
Chastre, et al: Comparison of 8 vs 15 days of antibiotic therapy for ventilator-associated pneumonia in adults: a randomized trial; JAMA, 2003, vol. 290(19), pp. 2588-2598.
El Solh: Update on the treatment of *Pseudomonas aeruginosa* pneumonia; J Antimicrob Chemother, 2009, vol. 64, pp. 229-238.
Zosyn®. Prescribing Information. Wyeth Pharmaceuticals, Inc., Philadelphia, PA, USA; http://labeling.pfizer.com/showlabeling.aspx?id=416 (Apr. 23, 2012, date last accessed), 26 pages.
Harrison's Principles of Internal Medicine: Hospital-Acquired (Nosocomial) Pneumonia; ed. Kasper, et al.; 16th ed. New York: McGraw-Hill, Medical Pub. Division. 2005, pp. 1538-1541.
Jones, et al: Microbial etiologies of hospital-acquired bacterial pneumonia and ventilator-associated bacterial pneumonia; Clin Infect Dis; 2010, Suppl 1, pp. S81-S87.
Joseph, et al: Ventilator-associated pneumonia: A Review; Eur J Intern Med; 2010, vol. 21(5), pp. 360-368.
Klevens, et al: Estimating health care-associated infections and deaths in U.S. hospitals, 2002; Public Health Rep, 2007, vol. 122, pp. 160-166.
Knaus, et al: APACHE II: A severity of disease classification system; Crit Care Med, 1985, vol. 13, pp. 818-829.
Komuro, et al: Inhibition of the renal excretion of tazobactam by piperacillin; J Antimicrob Chemother, 1994, vol. 34, pp. 555-564.
Mesaros, et al: *Pseudomonas aeruginosa*: resistance and therapeutic options at the turn of the new millennium; Clin Microbiol Infect, 2007, vol. 13, pp. 560-578.
International Search Report, PCT/US2012/054191, dated May 2, 2013, 4 pages.
Occhipinti, et al: Pharmacokinetics and pharmacodynamics of two multiple-dose piperacillin-tazobactam regimens; Antimicrob Agents Chemother, 1997, vol. 41, pp. 2511-2517.
PEA: The antimicrobial therapy puzzle: could pharmacokinetic-pharmacodynamic relationships be helpful in addressing the tissue of appropriate pneumonia treatment in critically ill patients?; Clin Infect Dis, 2006, vol. 42, pp. 1761-1771.
Richards, et al: Nosocomial infections in medical intensive care units in the United States. National Nosocomial Infections Surveillance Systems; Crit Care Med, 1999, vol. 27(5), pp. 887-892.
Freire, et al: Comparison of tigecycline with imipenem/cilastatin for the treatment of hospital-acquired penumonia; Diag Microbio and Infect Dis, 2010, vol. 68, pp. 140-151.
Schulgen, et al: Estimation of extra hospital stay attributable to nosocomial infections: heterogeneity and timing of events; J Clin Epidemiol; Apr. 2000, vol. 53(4), pp. 409-417.
Singh:et al: Short-course empiric antibiotic therapy for patients with pulmonary infiltrates in the intensive care unit. A proposed solution for indiscriminate antibiotic prescription; Am J Respir Crit Care Med, Aug. 2000, vol. 162(2, Pt 1), pp. 505-511.
Udy, et al: Augmented renal clearance: implications for antibacterial dosing in the critically ill; Clin Pharmacokinet, 2010, vol. 49(1), pp. 1-16.
Vincent, et al: Use of the SOFA score to assess the incidence of organ dysfunction/failure in intensive care units: results of a multicenter, prospective study. Working group on "sepsis-related problems" of the European Society of Intensive Care Medicine; Crit Care Med, 1998, vol. 26(11), pp. 1793-1800.
Wunderink, et al: Linezolid in methicillin-resistant *Staphylococcus aureus* nosocomial pneumonia: a randomized, controlled study; Clin Infect Dis, 2012, vol. 54(5), pp. 621-629.
Zilberberg, et al: Epidemiology of healthcare-associated pneumonia (HCAP); Semin Respir Crit Care Med, 2009, vol. 30, pp. 10-15.
Lucasti: A Phase 3, Randomized, Double-Blind Study of Ceftobiprole Medocaril Versus Linezolid Plus Ceftazidime in the Treatment of Nosocomial Pneumonia; Ceftobiprole: Clinical Study Report Synopsis BAP00248/307; Issue Date: Jul. 14, 2010; Document No. EDMS-PSDB-6906024:3.0, (8 pages).
Pankey: Tigecycline; J Antimicrob Chemotherapy, 2005, vol. 56, pp. 470-480.
Clinical Laboratory Standards Institute CLSI Document M100-S22; "Performance Standards for Antimicrobial Susceptibility Testing; Twenty-Second Informational Supplement"; Jan. 2012, vol. 32, No. 3, 188 pages.
Clinical Laboratory Standards Institute CLSI Document M07-A9; "Methods for Dilution Antimicrobial Susceptibility Tests for Bacteria That Grow Aerobically; Approved Standard—Ninth Edition"; Jan. 2012, vol. 32, No. 2., 88 pages.

TAZOBACTAM ARGININE COMPOSITIONS

RELATED APPLICATIONS

This application is a continuation of U.S. patent application Ser. No. 13/628,742, the contents of which are incorporated herein by reference.

TECHNICAL FIELD

This disclosure relates to solid forms of (2S,3S,5R)-3-((1H-1,2,3-triazol-1-yl)methyl)-3-methyl-7-oxo-4-thia-1-azabicyclo[3.2.0]heptane-2-carboxylic acid 4,4-dioxide (tazobactam), and related compositions and methods.

BACKGROUND

The crystal state of a compound may be important when the compound is used for pharmaceutical purposes. Compared with an amorphous solid, the solid physical properties of a crystalline compound may change, which may affect its suitability for pharmaceutical use. For example, a particular crystalline compound may overcome the disadvantage of other solid forms of the compound that readily absorb moisture (e.g., high hygroscopicity). For an ionic drug substance, high hygroscopicity may diminish the drug product's stability profile by a host of mechanisms, as the drug substance may have a propensity to absorb water. Water that is absorbed from the environment (packaging materials, exposure to air, or in the case of formulated products, from other materials), may lead to degradation products and/or impurities in a drug product or add to the cost of manufacturing the drug product with acceptably low levels of water.

One compound that can be obtained in amorphous or various crystalline salt forms is (2S,3S,5R)-3-((1H-1,2,3-triazol-1-yl)methyl)-3-methyl-7-oxo-4-thia-1-azabicyclo[3.2.0]heptane-2-carboxylic acid 4,4-dioxide, or tazobactam. There is a need for solid forms of tazobactam with reduced hygroscopicity for use in drug substance and drug product development.

SUMMARY

Solid forms of tazobactam (e.g., arginine salt forms of tazobactam) and compositions comprising these solid forms, are provided herein, in addition to various methods of preparing these compositions. Compared with previous crystalline forms of tazobactam, certain crystalline tazobactam arginine solid forms are provided herein that have the advantageous characteristic of being less hygroscopic. These crystalline tazobactam arginine solid forms can have good thermal stability and light stability in the process of preparation, packing, transportation and storage. Crystalline compounds of tazobactam arginine can also possess other properties that may be beneficial to the preparation of various drug formulations.

Crystalline tazobactam arginine, and hydrates and solvates thereof, can be obtained in various solid forms. Tazobactam arginine can be a salt consisting of the conjugate base of (2S,3S,5R)-3-((1H-1,2,3-triazol-1-yl)methyl)-3-methyl-7-oxo-4-thia-1-azabicyclo[3.2.0]heptane-2-carboxylic acid 4,4-dioxide (tazobactam) and the conjugate acid of (S)-2-amino-5-guanidinopentanoic acid (L-arginine) in a 1:1 ratio, as represented by the structure below.

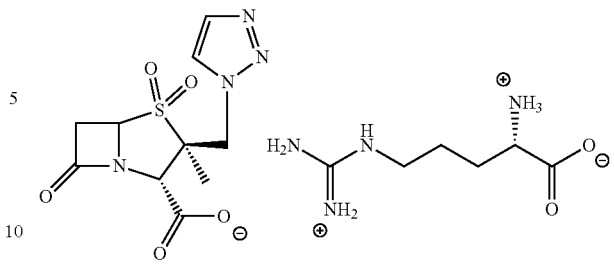

In one aspect, provided herein is a particularly preferred crystalline tazobactam arginine solid form (designated herein as "polymorph Ia" or "tazobactam arginine polymorph Ia"), characterized by an X-ray powder diffraction pattern having peaks expressed in degrees 2-Theta at angles of 4.8°±0.3°, 8.9°±0.3°, 11.3°±0.3°, 14.9°±0.3°, 18.0°±0.3°, 19.4°±0.3°, 21.3°±0.3°, 22.8°±0.3°, and 24.3°±0.3°. The crystalline tazobactam arginine can be further characterized by a differential scanning calorimetry thermogram having a characteristic peak expressed in units of ° C. at a temperature of 209.2±3. In another embodiment, the crystalline tazobactam arginine is further characterized by a thermogravimetry curve with an onset temperature of 201.9° C.±3° C.

Also provided are pharmaceutical compositions comprising a compound having a beta-lactam chemical sub-structure (e.g., a beta-lactam antibiotic compound) and crystalline tazobactam arginine (e.g., of the polymorph Ia solid form).

In another aspect, provided herein is a method for the treatment of bacterial infections in a mammal, comprising administering to said mammal a therapeutically effective amount of a crystalline tazobactam arginine compound (e.g., of the polymorph Ia solid form). The crystalline tazobactam arginine can be characterized by an X-ray powder diffraction pattern having peaks expressed in degrees 2-Theta at angles of 4.8°±0.3°, 8.9°±0.3°, 11.3°±0.3°, 14.9°±0.3°, 18.0°±0.3°, 19.4°±0.3°, 21.3°±0.3°, 22.8°±0.3° and 24.3°±0.3°.

In another aspect, provided herein is a method for the treatment of bacterial infections in a mammal, comprising administering to said mammal a therapeutically effective amount of a pharmaceutical composition comprising an beta-lactam compound and a crystalline tazobactam arginine compound (e.g., of the polymorph Ia solid form). The crystalline tazobactam arginine can be characterized by an X-ray powder diffraction pattern having peaks expressed in degrees 2-Theta at angles of 4.8°±0.3°, 8.9°±0.3°, 11.3°±0.3°, 14.9°±0.3°, 18.0°±0.3°, 19.4°±0.3°, 21.3°±0.3°, 22.8°±0.3° and 24.3°±0.3°.

In another aspect, provided herein is a method for detecting or identifying an agent that inhibits one or more beta-lactamase-producing organisms, said method comprising combining:

(a) a test agent;
(b) a composition comprising one or more beta-lactamase-producing organisms; and
(c) crystalline tazobactam arginine, wherein the crystalline tazobactam arginine is characterized by an X-ray powder diffraction pattern having peaks expressed in degrees 2-Theta at angles of 4.8°±0.3°, 8.9°±0.3°, 11.3°±0.3°, 14.9°±0.3°, 18.0°±0.3°, 19.4°±0.3°, 21.3°±0.3°, 22.8°±0.3° and 24.3°±0.3°; and detecting or measuring a change in the activity of the beta-lactamase-producing organisms, wherein a decrease in the activity of the beta-lactamase-producing organisms indicates that the test agent inhibits the beta-lactamase-producing organisms.

DETAILED DESCRIPTION

Figure 1:
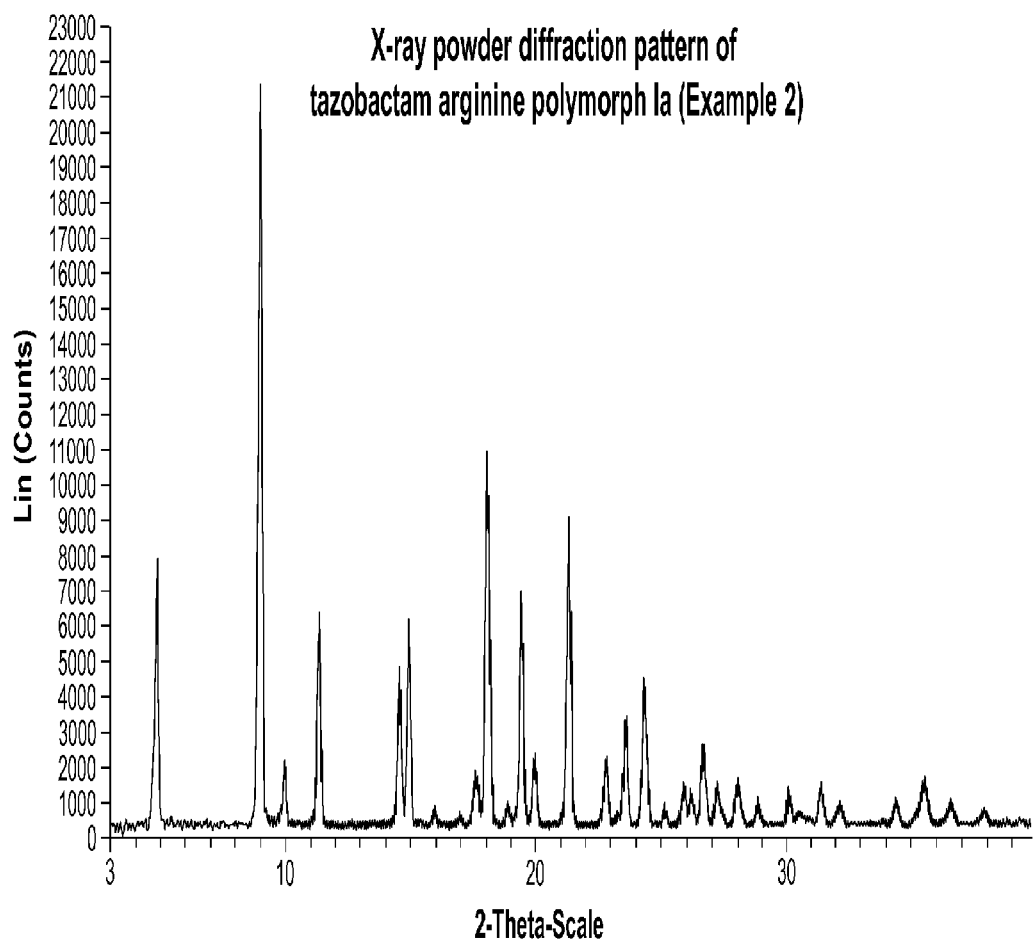
FIG. 1 depicts the X-ray powder diffraction pattern of polymorph Ia (Example 2).

Tazobactam arginine may occur in an amorphous solid form or in a crystalline solid form. Crystalline solid forms of tazobactam arginine may exist in one or more unique polymorph forms, which may additionally comprise one or more equivalents of water or solvent (i.e., hydrates or solvates, respectively).

Tazobactam arginine is the salt of the conjugate base of tazobactam and the conjugate acid of (S)-2-amino-5-guanidinopentanoic acid (L-arginine) in a 1:1 ratio, as represented by the structure below.

Accordingly, provided herein is crystalline tazobactam arginine, and hydrates and solvates thereof. In particular, provided herein is crystalline tazobactam arginine polymorph Ia, also referred to herein as "polymorph Ia" or "tazobactam arginine polymorph Ia", and crystalline tazobactam arginine polymorph Ib, also referred to herein as "polymorph Ib" or "tazobactam arginine polymorph Ib".

Polymorphism

The ability of a substance to exist in more than one crystal form is defined as polymorphism; the different crystal forms of a particular substance are referred to as "polymorphs." In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs. In contrast, the overall external form of a substance is known as "morphology," which refers to the external shape of the crystal and the planes present, without reference to the internal structure. Crystals can display different morphology based on different conditions, such as, for example, growth rate, stirring, and the presence of impurities.

The different polymorphs of a substance can possess different energies of the crystal lattice and, thus, in solid state they can show different physical properties such as form, density, melting point, color, stability, solubility, dissolution rate, etc., which can, in turn, affect the stability, dissolution rate and/or bioavailability of a given polymorph and its suitability for use as a pharmaceutical and in pharmaceutical compositions.

Access to different polymorphs of tazobactam arginine is desirable for other reasons as well. One such reason is that different polymorphs of a compound (e.g., tazobactam arginine) can incorporate different impurities, or chemical residues, upon crystallization. Certain polymorphs incorporate very little, or no, chemical residues. Accordingly, the formation of certain polymorph forms of a compound may result in purification of the compound.

Tazobactam arginine polymorph Ia exhibits low hygroscopicity relative to amorphous tazobactam arginine and amorphous tazobactam sodium. Low hygroscopicity of a solid compound is desirable for several reasons. For example, compounds that are highly hygroscopic may be chemically unstable, or unsuitable for formulating as a drug product due to changes of the drug form's physical characteristics (e.g., bulk density, dissolution rate, etc.) that can occur if it is stored in settings with varying relative humidity. Also, hygroscopicity can impact large-scale manufacturing and handling of a compound. For example, it may be difficult to determine the true weight of a hygroscopic active agent when preparing a pharmaceutical composition comprising that agent.

Characterization of Polymorphs

In certain embodiments, the compounds of the invention are identifiable on the basis of characteristic peaks in an X-ray powder diffraction analysis. X-ray powder diffraction, also referred to as XRPD, is a scientific technique using X-ray, neutron, or electron diffraction on powder, microcrystalline, or other solid materials for structural characterization of the materials.

One embodiment of crystalline tazobactam arginine is referred to as polymorph Ia (also referred to herein as "tazobactam arginine polymorph Ia") and is characterized by an X-ray powder diffraction pattern having one or more characteristic peaks expressed in degrees 2-Theta at angles selected from 8.9°±0.3°, 18.0°±0.3° and 21.3°±0.3°. In another embodiment, polymorph Ia is characterized by an X-ray powder diffraction pattern having one or more peaks expressed in degrees 2-Theta at angles selected from 4.8°±0.3°, 11.3°±0.3° and 14.9°±0.3°. In still another embodiment, polymorph Ia is characterized by an X-ray powder diffraction pattern having one or more peaks expressed in degrees 2-Theta at angles selected from 19.4°±0.3°, 22.8°±0.3° and 24.3°±0.3°.

In another embodiment, polymorph Ia is characterized by an X-ray powder diffraction pattern having 3-6 peaks expressed in degrees 2-Theta at angles selected from 8.9°±0.3°, 18.0°±0.3°, 21.3°±0.3°, 4.8°±0.3°, 11.3°±0.3°, 14.9°±0.3°, 19.4°±0.3°, 22.8°±0.3° and 24.3°±0.3°. In a particular embodiment, polymorph Ia is characterized by an X-ray powder diffraction pattern having characteristic peaks expressed in degrees 2-Theta at angles of 8.9°±0.3°, 18.0°±0.3° and 21.3°±0.3°.

In yet another embodiment, polymorph Ia is characterized by an X-ray powder diffraction pattern having 3-6 peaks expressed in degrees 2-Theta at angles selected from 8.9°±0.2°, 18.0°±0.2°, 21.3°±0.2°, 4.8°±0.2°, 11.3°±0.2°, 14.9°±0.2°, 19.4°±0.2°, 22.8°±0.2° and 24.3°±0.2°. In a particular embodiment, polymorph Ia is characterized by an X-ray powder diffraction pattern having characteristic peaks expressed in degrees 2-Theta at angles of 8.9°±0.2°, 18.0°±0.2° and 21.3°±0.2°.

In still another embodiment, polymorph Ia is characterized by an X-ray powder diffraction pattern having 6-9 peaks expressed in degrees 2-Theta at angles selected from 8.9°±0.3°, 18.0°±0.3°, 21.3°±0.3°, 4.8°±0.3°, 11.3°±0.3°, 14.9°±0.3°, 19.4°±0.3°, 22.8°±0.3° and 24.3°±0.3°. In a particular embodiment, polymorph Ia is characterized by an X-ray powder diffraction pattern having characteristic peaks expressed in degrees 2-Theta at angles of 4.8°±0.3°, 8.9°±0.3°, 11.3°±0.3°, 14.9°±0.3°, 18.0°±0.3°, 19.4°±0.3°, 21.3°±0.3° 22.8°±0.3° and 24.3°±0.3°.

In still another embodiment, polymorph Ia is characterized by an X-ray powder diffraction pattern having 6-9 peaks expressed in degrees 2-Theta at angles selected from 8.9°±0.2°, 18.0°±0.2°, 21.3°±0.2°, 4.8°±0.2°, 11.3°±0.2°, 14.9°±0.2°, 19.4°±0.2°, 22.8°±0.2° and 24.3°±0.2°. In a particular embodiment, polymorph Ia is characterized by an X-ray powder diffraction pattern having characteristic peaks expressed in degrees 2-Theta at angles of 4.8°±0.2°, 8.9°±0.2°, 11.3°±0.2°, 14.9°±0.2°, 18.0°±0.2°, 19.4°±0.2°, 21.3°±0.2° 22.8°±0.2°and 24.3°±0.2°.

In still another embodiment, provided herein is a composition comprising crystalline tazobactam arginine characterized by an X-ray powder diffraction pattern having peaks expressed in degrees 2-Theta±0.3° at angles of 4.8°, 8.9°, 11.3°, 14.9°, 18.0°, 19.4°, 21.3°, 22.8° and 24.3°.

In still another embodiment, provided herein is a composition comprising crystalline tazobactam arginine characterized by an X-ray powder diffraction pattern having peaks expressed in degrees 2-Theta±0.2° at angles of 4.8°, 8.9°, 11.3°, 14.9°, 18.0°, 19.4°, 21.3°, 22.8° and 24.3°.

In still another embodiment, provided herein is a composition comprising crystalline tazobactam arginine characterized by an X-ray powder diffraction pattern having peaks expressed in degrees 2-Theta±0.1° at angles of 4.8°, 8.9°, 11.3°, 14.9°, 18.0°, 19.4°, 21.3°, 22.8° and 24.3°.

In still another embodiment, provided herein is a composition comprising crystalline tazobactam arginine characterized by an X-ray powder diffraction pattern having peaks expressed in degrees 2-Theta at angles of about 4.8°, 8.9°, 11.3°, 14.9°, 18.0°, 19.4°, 21.3°, 22.8° and 24.3°.

In one embodiment, polymorph Ia is characterized by an X-ray powder diffraction pattern having peaks substantially in accordance with FIG. 1. In another embodiment, polymorph Ia is characterized by an X-ray powder diffraction pattern having peaks substantially in accordance with Table 1.

Figure 2:
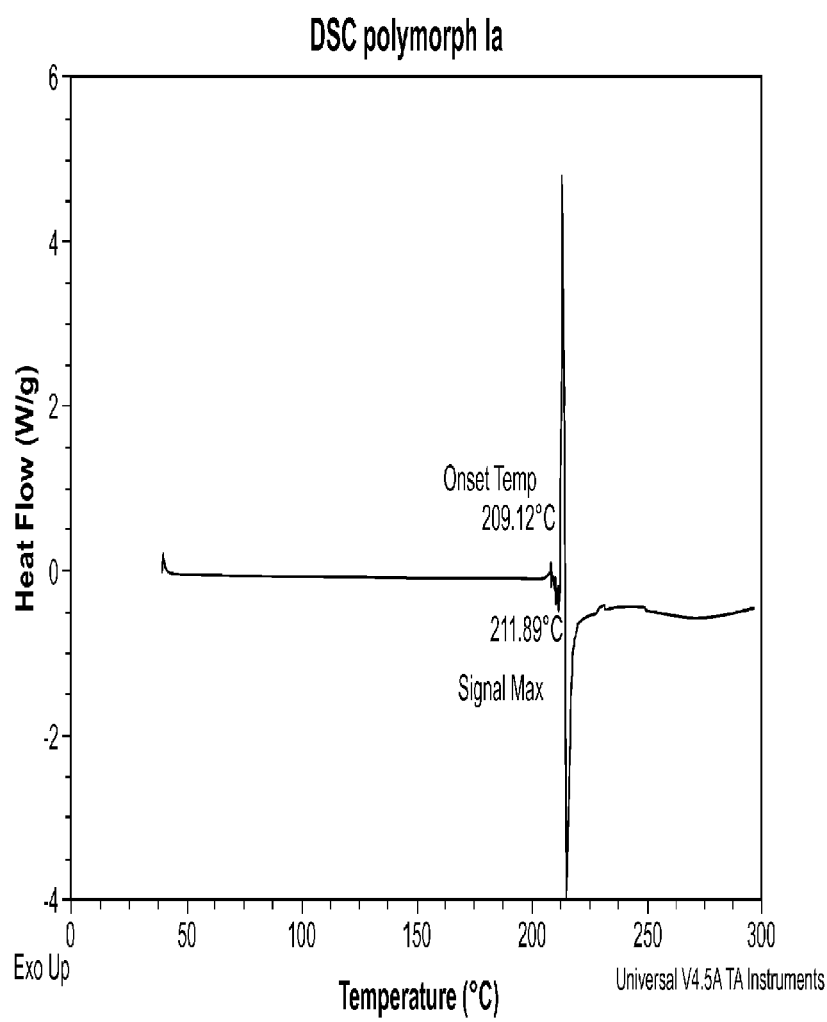
FIG. 2 depicts the differential scanning calorimetry (DVS) thermogram of polymorph Ia.

The compounds of the invention may also be defined by their differential scanning calorimetry (DSC) thermograms. In one embodiment, polymorph Ia is characterized by a differential scanning calorimetry thermogram having a characteristic peak expressed in units of ° C. at a temperature of 209.2±3. In a particular embodiment, polymorph Ia is characterized by a differential scanning calorimetry thermogram substantially in accordance with FIG. 2.

Figure 3:
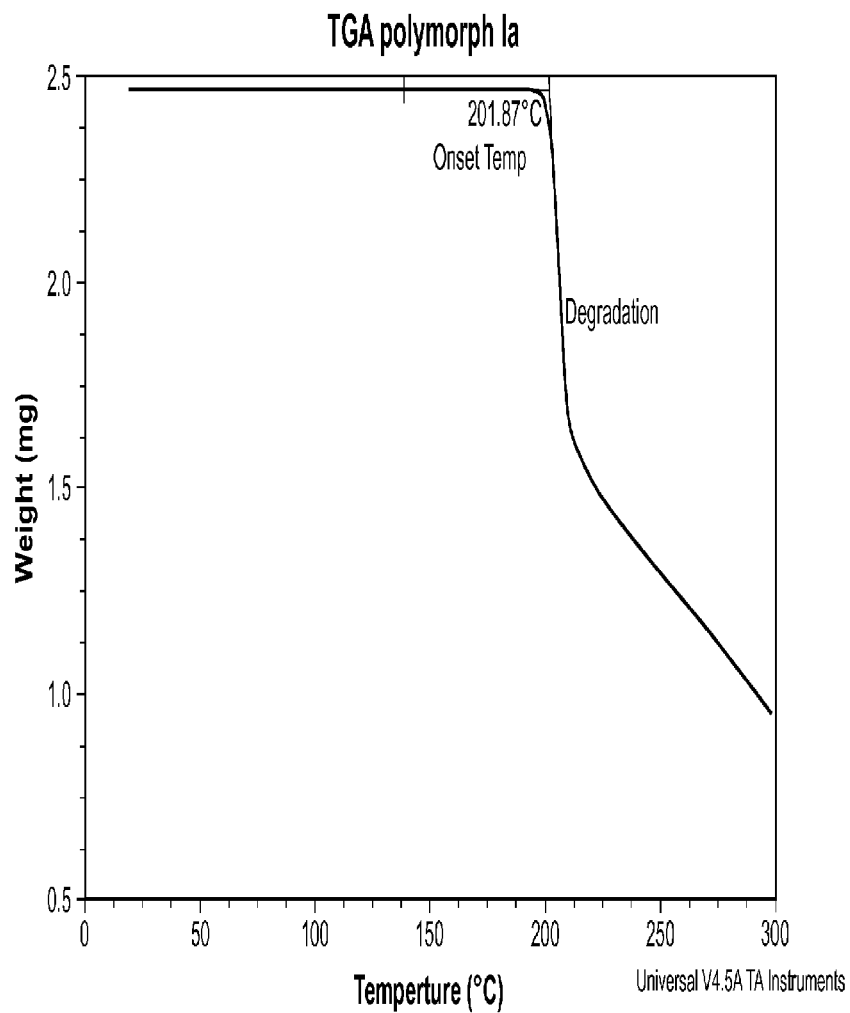
FIG. 3 depicts the thermogravimetry curve of polymorph Ia.

The compounds of the invention can be also be defined by their thermogravimetry (TG) signals. In one embodiment, polymorph Ia is characterized by a thermogravimetry curve with an onset temperature of 201.8° C.±3° C. In a particular embodiment, polymorph Ia is characterized by a thermogravimetry curve substantially in accordance with FIG. 3.

In certain embodiments, polymorph Ia may contain impurities. Non-limiting examples of impurities include undesired polymorph forms, or residual organic and inorganic molecules such as solvents, water or salts.

In another embodiment, polymorph Ia is substantially free from impurities. In another embodiment, polymorph Ia contains less than 10% by weight total impurities. In another embodiment, polymorph Ia contains less than 5% by weight total impurities. In another embodiment, polymorph Ia contains less than 1% by weight total impurities. In yet another embodiment, polymorph Ia contains less than 0.1% by weight total impurities.

Figure 4:
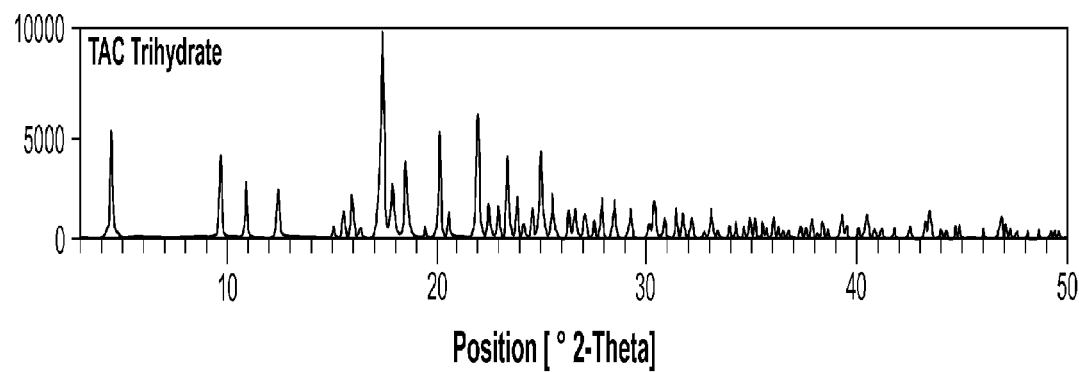
FIG. 4 depicts the X-ray powder diffraction pattern of polymorph Ib.

In another aspect, provided herein is crystalline tazobactam arginine polymorph Ib. In one embodiment, polymorph Ib is tazobactam arginine trihydrate. In another embodiment, crystalline tazobactam polymorph Ib is characterized by an X-ray powder diffraction pattern having peaks expressed in degrees 2-Theta at angles of 4.4°±0.3°, 9.7°±0.3°, 17.3°±0.3°, 20.2°±0.3°, and 22.0°±0.3°. In a particular embodiment, polymorph Ib is characterized by an X-ray powder diffraction pattern having peaks substantially in accordance with FIG. 4.

In another aspect, provided herein is a composition comprising one or more compounds selected from amorphous tazobactam arginine, polymorph Ia and polymorph Ib. In one embodiment, the composition comprises one or more compounds selected from tazobactam arginine and polymorph Ia.

In certain embodiments, polymorph Ia is a crystalline solid substantially free of amorphous tazobactam arginine. As used herein, the term "substantially free of amorphous tazobactam arginine" means that the compound contains no significant amount of amorphous tazobactam arginine. In certain embodiments, at least about 95% by weight of crystalline polymorph Ia is present. In still other embodiments of the invention, at least about 99% by weight of crystalline polymorph Ia is present.

In another embodiment, polymorph Ia is substantially free from polymorph Ib. As used herein, the term "substantially free of polymorph Ib" means that the compound contains no significant amount of polymorph Ib. In certain embodiments, at least about 95% by weight of crystalline polymorph Ia is present. In still other embodiments of the invention, at least about 99% by weight of crystalline polymorph Ia is present.

Processes and Methods

Provided herein is a method of making crystalline tazobactam arginine comprising:

(1) combining tazobactam acid, arginine and a solvent, such that a solution of tazobactam arginine is formed; and (2) combining an antisolvent with the solution, wherein the antisolvent is miscible with the solvent and wherein tazobactam arginine is partially or completely insoluble in the antisolvent, such that crystalline tazobactam arginine precipitates from the solution.

In step (1), tazobactam acid may first be combined with the solvent, and the resulting mixture then combined with arginine. Alternatively, arginine may first be combined with the solvent, and the resulting mixture then combined with tazobactam acid. Alternatively, tazobactam acid and arginine may be combined, and the resulting mixture then combined with the solvent.

In one embodiment, the above method is a method of making tazobactam arginine polymorph Ia, said method further comprising: (3) drying the precipitated crystalline tazobactam arginine to afford polymorph Ia.

In one embodiment, the antisolvent is added to the solution of tazobactam arginine. In another embodiment, the solution of tazobactam argine is added to the antisolvent. In certain embodiments, the solvent is selected from the group consisting of water and acetic acid. In certain embodiments, the antisolvent is selected from the group consisting of alcohols, ethers, esters, ketones, nitriles, amides, nitroalkanes, nitroarenes, substituted or unsubstituted aromatic solvents, substituted or unsubstituted aliphatic solvents and mixtures thereof. In certain embodiments, the antisolvent is selected from the group consisting of acetone, acetonitrile, 1-butanol, cyclohexane, dichloromethane, diisopropyl ether, dimethylformamide, dimethylsulfoxide, 1,4-dioxane, ethanol, ethyl acetate, heptanes, methanol, isopropyl acetate, methyl ethyl ketone, methyl isobutyl ketone, N-methyl-2-pyrrolidinone, nitromethane, 2-propanol, tert-butylmethyl ether, tetrahydrofuran, toluene and mixtures thereof. Experiments determining solubility of crystalline tazobactam arginine in a variety of solvents are described in Experiment 6, and results are summarized in Table 3. In a preferred embodiment, the solvent is water. In another preferred embodiment, the antisolvent is acetone. In yet another preferred embodiment, the antisolvent is isopropanol.

Accordingly, provided herein is a method of making crystalline tazobactam arginine comprising:

(1) combining tazobactam acid, arginine and water, such that an aqueous solution of tazobactam arginine is formed; and (2) combining acetone with the aqueous solution, such that crystalline tazobactam arginine precipitates from the solution.

In one embodiment, the above method is a method of making tazobactam arginine polymorph Ia, said method further comprising: (3) drying the precipitated crystalline tazobactam arginine to afford polymorph Ia.

In another aspect, provided herein is a method of making crystalline tazobactam arginine (e.g., polymorph Ia) comprising:

(1) combining tazobactam arginine and a solvent, such that a solution of tazobactam arginine is formed; and (2) combining an antisolvent with the solution, wherein the antisolvent is miscible with the solvent and wherein tazobactam arginine is partially or completely insoluble in the antisolvent, such that crystalline tazobactam arginine precipitates from the solution.

In another aspect, provided herein is a method of making crystalline tazobactam arginine comprising:

(1) combining tazobactam acid, arginine and a solvent/antisolvent mixture, such that a solution of tazobactam arginine is formed; and (2) combining an antisolvent with the solution, wherein the antisolvent is miscible with the solvent and wherein tazobactam arginine is partially or completely insoluble in the antisolvent, such that crystalline tazobactam arginine precipitates from the solution.

In certain embodiments, any one of the above methods is a method of making tazobactam arginine polymorph Ia and the method further comprises: (3) drying the precipitated crystalline tazobactam arginine to afford polymorph Ia.

In another aspect, provided herein is a method of making crystalline tazobactam arginine comprising:

(1) combining a compound according to formula (I), a compound according to formula (II), and a solvent, such that a solution comprising tazobactam arginine is formed, and such that crystalline tazobactam arginine precipitates from the solution.

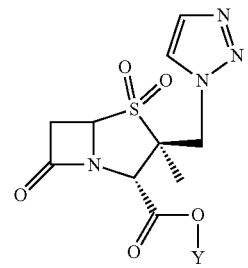

(I)

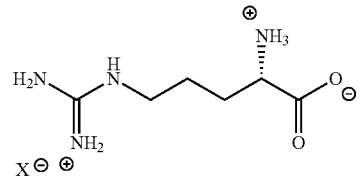

(II)

In one embodiment, Y is a metal atom or ion and X— is a halide ion.

In still another aspect, provided herein is a method of making crystalline tazobactam arginine comprising:

(1) combining a compound according for formula (I), a compound according to formula (II), and a solvent, such that a solution comprising tazobactam arginine is formed; and (2) combining an antisolvent with the solution, wherein the antisolvent is miscible with the solvent and wherein tazobactam arginine is partially or completely insoluble in the antisolvent, such that crystalline tazobactam arginine precipitates from the solution. In one embodiment, Y is a metal atom or ion and X— is a halogen ion.

In another aspect, provided herein is crystalline tazobactam arginine produced according to the any one of the preceding methods. In another aspect, provided herein is crystalline tazobactam arginine obtainable by any one of the preceding methods.

The processes and methods described herein may also further comprise adding one or more seed crystals of crystalline tazobactam arginine (e.g., polymorph Ia or polymorph Ib).

As used herein, the verb "precipitate" refers to the formation of a solid substance from a solution containing the same substance. A substance which precipitates from solution may be amorphous or crystalline. Precipitation may occur under a variety of conditions known to those of skill in the art, including the treatment of a solution of a solute (e.g., solute A in solvent B) with an antisolvent (i.e., a solvent that is miscible with solvent B, but does not dissolve solute A). Non-limiting examples of solvent/antisolvent pairs include water/acetone and water/isopropanol.

Pharmaceutical Compositions

In one aspect, provided herein is a pharmaceutical composition comprising tazobactam arginine polymorph Ia.

In another aspect, provided herein is a pharmaceutical composition comprising crystalline tazobactam arginine, hydrates or solvates thereof, and one or more beta-lactam compounds, and a pharmaceutically acceptable carrier or diluent. In one embodiment, the pharmaceutical composition is useful for treating a bacterial infection. The bacterial infection can result from either gram-negative or gram-positive organisms. In one embodiment, the crystalline tazobactam arginine is polymorph Ia. Polymorph Ia is characterized as described above.

In yet another aspect, provided herein is a pharmaceutical composition prepared by a method comprising the step of combining crystalline tazobactam arginine, or hydrates or solvates thereof, and a beta-lactam compound. In one embodiment, the crystalline tazobactam arginine is polymorph Ia. Polymorph Ia is characterized as described above.

A "beta-lactam compound" is a compound possessing one or more beta-lactam moieties, i.e.,

substituted one or more times as valency permits. In certain non-limiting embodiments the beta-lactam compounds described herein can be selected from the group consisting of penicillins, cephalosporins, carbapenems, and combinations thereof. In certain embodiments, said one or more beta-lactam compounds are selected from the compounds listed in Table 2, and pharmaceutically acceptable isomers, salts, esters, hydrates, solvates, or combinations thereof.

The following compounds are listed in Table 2:
- (2S,5R,6R)-6-[(R)-2-(4-ethyl-2,3-dioxo-1-piperazinecarboxamido)-2-phenylacetamido]-3,3-dimethyl-7-oxo-4-thia-1-azabicyclo[3.2.0]heptane-2-carboxylic acid;
- (2S,5R,6R)-3,3-dimethyl-7-oxo-6-(2-phenylacetamido)-4-thia-1-zabicyclo[3.2.0]heptane-2-carboxylic acid;
- (5R,6S)-6-[(1R)-1-hydroxyethyl]-3-({2-[(iminomethyl)amino]ethyl}thio)-7-oxo-1-azabicyclo[3.2.0]hept-2-ene-2-carboxylic acid;
- (5R,6S)-6-((R)-1-hydroxyethyl)-7-oxo-3-((R)-tetrahydrofuran-2-yl)-4-thia-1-azabicyclo[3.2.0]hept-2-ene-2-carboxylic acid;
- (2S,5R,6R)-6-{[3-(2-chlorophenyl)-5-methyl-oxazole-4-carbonyl]amino}-3,3-dimethyl-7-oxo-4-thia-1-azabicyclo[3.2.0]heptane-2-carboxylic acid;
- (6R,7R,Z)-7-(2-(2-aminothiazol-4-yl)-2-(2-carboxypropan-2-yloxyimino)acetamido)-8-oxo-3-(pyridinium-1-ylmethyl)-5-thia-1-aza-bicyclo[4.2.0]oct-2-ene-2-carboxylate;
- 6R,7R,Z)-3-(acetoxymethyl)-7-(2-(2-aminothiazol-4-yl)-2-(methoxyimino)acetamido)-8-oxo-5-thia-1-azabicyclo[4.2.0]oct-2-ene-2-carboxylic acid;
- (6R,7R)-7-[(2Z)-2-ethoxyimino-2-[5-(phosphonoamino)-1,2,4-thiadiazol-3-yl]acetyl]amino]-3-[4-(1-methylpyridin-1-ium-4-yl)-1,3-thiazol-2-yl]sulfanyl]-8-oxo-5-thia-1-azabicyclo[4.2.0]oct-2-ene-2-carboxylate;
- (6R,7R,Z)-7-(2-(2-aminothiazol-4-yl)-2-(methoxyimino)acetamido)-3-((1-methylpyrrolidinium-1-yl)methyl)-8-oxo-5-thia-1-aza-bicyclo[4.2.0]oct-2-ene-2-carboxylate;
- (6R,7R)-3-{[(aminocarbonyl)oxy]methyl}-7-{[(2Z)-2-(2-furyl)-2-(methoxyimino) acetyl]amino}-8-oxo-5-thia-1-azabicyclo[4.2.0]oct-2-ene-2-carboxylic acid;
- (6R,7R)-7-{[(2Z)-2-(2-amino-1,3-thiazol-4-yl)-2-(methoxyimino)acetyl]amino}-3-{[(2-methyl-5,6-dioxo-1,2,5,6-tetrahydro-1,2,4-triazin-3-yl)thio]methyl}-8-oxo-5-thia-1-azabicyclo[4.2.0]oct-2-ene-2-carboxylic acid;
- (2S,5R,6R)-6-{-[(2R)-2-amino-2-(4-hydroxyphenyl)-acetyl]amino}-3,3-dimethyl-7-oxo-4-thia-1-azabicyclo[3.2.0]heptane-2-carboxylic acid;
- 3-[5-(dimethylcarbamoyl)pyrrolidin-2-yl]sulfanyl-6-(1-hydroxyethyl)-4-methyl-7-oxo-1-azabicyclo[3.2.0]hept-2-ene-2-carboxylic acid.

In a particular embodiment, the pharmaceutical composition comprises polymorph Ia and (2S,5R,6R)-3,3-dimethyl-7-oxo-6-(2-phenylacetamido)-4-thia-1-zabicyclo[3.2.0]heptane-2-carboxylic acid or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (5R,6S)-6-[(1R)-1-hydroxyethyl]-3-({2-[(iminomethyl)amino]ethyl} thio)-7-oxo-1-azabicyclo[3.2.0]hept-2-ene-2-carboxylic acid, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (5R,6S)-6-((R)-1-hydroxyethyl)-7-oxo-3-((R)-tetrahydrofuran-2-yl)-4-thia-1-azabicyclo[3.2.0]hept-2-ene-2-carboxylic acid, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (2S,5R,6R)-6-{[3-(2-chlorophenyl)-5-methyl-oxazole-4-carbonyl]amino}-3,3-dimethyl-7-oxo-4-thia-1-azabicyclo[3.2.0]heptane-2-carboxylic acid, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (6R,7R,Z)-7-(2-(2-aminothiazol-4-yl)-2-(2-carboxypropan-2-yloxyimino)acetamido)-8-oxo-3-(pyridinium-1-ylmethyl)-5-thia-1-aza-bicyclo[4.2.0]oct-2-ene-2-carboxylate, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (6R,7R,Z)-3-(acetoxymethyl)-7-(2-(2-aminothiazol-4-yl)-2-(methoxyimino)acetamido)-8-oxo-5-thia-1-azabicyclo[4.2.0]oct-2-ene-2-carboxylic acid, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (6R,7R)-7-[(2Z)-2-ethoxyimino-2-[5-(phosphonoamino)-1,2,4-thiadiazol-3-yl]acetyl]amino]-3-[4-(1-methylpyridin-1-ium-4-yl)-1,3-thiazol-2-yl]sulfanyl]-8-oxo-5-thia-1-azabicyclo[4.2.0]oct-2-ene-2-carboxylate, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (6R,7R,Z)-7-(2-(2-aminothiazol-4-yl)-2-(methoxyimino)acetamido)-3-((1-methylpyrrolidinium-1-yl)methyl)-8-oxo-5-thia-1-aza-bicyclo[4.2.0]oct-2-ene-2-carboxylate, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (6R,7R)-3-{[(aminocarbonyl)oxy]methyl}-7-{[(2Z)-2-(2-furyl)-2-(methoxyimino) acetyl]amino}-8-oxo-5-thia-1-azabicyclo[4.2.0]oct-2-ene-2-carboxylic acid, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (6R,7R)-7-{[(2Z)-2-(2-amino-1,3-thiazol-4-yl)-2-(methoxyimino)acetyl]amino}-3-{[(2-methyl-5,6-dioxo-1,2,5,6-tetrahydro-1,2,4-triazin-3-yl)thio]methyl}-8-oxo-5-thia-1-azabicyclo[4.2.0]oct-2-ene-2-carboxylic acid, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (2S,5R,6R)-6-{[(2R)-2-amino-2-(4-hydroxyphenyl)-acetyl]amino}-3,3-dimethyl-7-oxo-4-thia-1-azabicyclo[3.2.0]heptane-2-carboxylic acid, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and (2S,5R,6R)-6-[(R)-2-(4-ethyl-2,3-dioxo-1-piperazinecarboxamido)-2-phenylacetamido]-3,3-dimethyl-7-oxo-4-thia-1-azabicyclo[3.2.0]heptane-2-carboxylic acid, or a pharmaceutically acceptable isomer, salt, ester, hydrate, solvate, or combination thereof, and a pharmaceutically acceptable carrier or diluent.

In another particular embodiment, the pharmaceutical composition comprises polymorph Ia and 3-[5-(dimethylcarbamoyl) pyrrolidin-2-yl]sulfanyl-6-(1-hydroxyethyl)-4-methyl-7-oxo-1-azabicyclo[3.2.0]hept-2-ene-2-carboxylic acid, or a pharmaceutically acceptable isomer, salt, ester, hydrate, solvate, or combination thereof, and a pharmaceutically acceptable carrier or diluent.

Pharmaceutical compositions comprising compounds of the invention can be identified by comparison of the compositions' X-ray powder diffraction patterns to an X-ray powder diffraction pattern of a compound of the invention. It will be appreciated that pharmaceutical compositions comprising a compound of the invention may exhibit non-identical X-ray powder diffraction patterns as compared to an X-ray powder diffraction pattern of a pure compound of the invention.

The term "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1% to 99.9% (more preferably, 0.5 to 90%) of active ingredient in combination with a pharmaceutically acceptable carrier.

The pharmaceutical compositions described herein can be formulated to have any concentration desired (i.e., any concentration of crystalline tazobactam arginine, or a hydrate or solvate thereof, and any concentration of a beta-lactam compound). In some embodiments, the composition is formulated such that it comprises at least a therapeutically effective amount of both compounds (i.e., a therapeutically effective amount of the combination of crystalline tazobactam arginine, or a hydrate or solvate thereof, and the beta-lactam compound). In some embodiments, the composition is formulated such that it would not cause one or more unwanted side effects.

The compounds of the invention (i.e., polymorphs, hydrates and solvates of tazobactam arginine) can be combined with a pharmaceutically acceptable carrier according to conventional pharmaceutical compounding techniques. As used herein, "pharmaceutically acceptable carrier" may include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Eighteenth Edition, A. R. Gennaro (Mack Publishing Co., Easton, Pa., 1990) discloses various carriers used in formulating pharmaceutical compositions and known techniques for the preparation thereof. Except insofar as any conventional carrier medium is incompatible with the compounds such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline ("normal saline"); Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, trehalose, or reducing or non-reducing sugars, 5% dextrose (D5W), preservatives and antioxidants can also be present in the composition, according to the judgment of the formulator.

Furthermore, the carrier may take a wide variety of forms depending on the form of the preparation desired for administration, e.g. oral, nasal, rectal, vaginal, parenteral (including intravenous injections or infusions). In preparing compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Pharmaceutical compositions include those suitable for oral, sublingual, nasal rectal, vaginal, topical, buccal and parenteral (including subcutaneous, intramuscular, and intravenous) administration, although the most suitable route will depend on the nature and severity of the condition being treated. The compositions may be conveniently presented in unit dosage form, and prepared by any of the methods well known in the art of pharmacy. In certain embodiments, the pharmaceutical composition is formulated for oral administration in the form of a pill, capsule, lozenge or tablet. In other embodiments, the pharmaceutical composition is in the form of a suspension.

The pharmaceutical compositions disclosed herein can be prepared via lyophilization. As is known to those skilled in the art, lyophilization is a process of drying in which water is sublimed from a frozen solution of one or more solutes. Specific methods of lyophilization are described in Remington's Pharmaceutical Sciences, Chapter 84, page 1565, Eighteenth Edition, A. R. Gennaro, (Mack Publishing Co., Easton, Pa., 1990).

In a preferred embodiment, pharmaceutical compositions comprising crystalline tazobactam arginine (e.g., polymorph Ia) and one or more beta-lactam compounds are formulated for parenteral administration. In another preferred embodiment, pharmaceutical compositions comprising tazobactam arginine and one or more beta-lactam compounds are formulated for oral administration.

Methods of Treatment

Tazobactam arginine inhibits or decreases the activity of beta-lactamases (e.g., bacterial beta-lactamases), and can be combined with beta-lactam compounds (e.g., antibiotics), thereby broadening the spectrum of the beta-lactam compound and increasing the beta-lactam compound's efficacy against organisms that produce beta-lactamase. A compound or a composition possesses efficacy against an organism if it kills or weakens the organism, or inhibits or prevents reproduction the organism.

In one aspect, provided herein is a method for the treatment of bacterial infections in a mammal, comprising administering to said mammal a therapeutically effective amount of tazobactam arginine polymorph Ia.

In another aspect, provided herein is a method for the treatment of bacterial infections in a mammal, comprising administering to said mammal a therapeutically effective amount of a pharmaceutical composition comprising tazobactam arginine polymorph Ia.

In yet another aspect, provided herein is a method for the treatment of bacterial infections in a mammal, comprising administering to said mammal a therapeutically effective amount of a pharmaceutical composition comprising crystalline tazobactam arginine and one or more beta-lactam compounds, or a pharmaceutically acceptable isomer, salt, ester, hydrate, solvate, or combination thereof. In one embodiment, the mammal is human. In another embodiment, tazobactam arginine is polymorph Ia. In yet another embodiment, said one or more beta-lactam compounds are selected from the group consisting of penicillins, cephalosporins, carbapenems, and combinations thereof. In certain embodiments, the beta-lactam compound is selected from the compounds listed in Table 2, and pharmaceutically acceptable isomers, salts, esters, hydrates, solvates, or combinations thereof.

The following compounds are listed in Table 2: (2S,5R,6R)-6-[(R)-2-(4-ethyl-2,3-dioxo-1-piperazinecarboxamido)-2-phenylacetamido]-3,3-dimethyl-7-oxo-4-thia-1-azabicyclo[3.2.0]heptane-2-carboxylic acid; (2S,5R,6R)-3,3-dimethyl-7-oxo-6-(2-phenylacetamido)-4-thia-1-zabicyclo[3.2.0]heptane-2-carboxylic acid; (5R,6S)-6-[(1R)-1-hydroxyethyl]-3-({2-[(iminomethyl)amino]ethyl}thio)-7-oxo-1-azabicyclo[3.2.0]hept-2-ene-2-carboxylic acid; (5R,6S)-6-((R)-1-hydroxyethyl)-7-oxo-3-((R)-tetrahydrofuran-2-yl)-4-thia-1-azabicyclo[3.2.0]hept-2-ene-2-carboxylic acid; (2S,5R,6R)-6-{[3-(2-chlorophenyl)-5-methyl-oxazole-4-carbonyl]amino}-3,3-dimethyl-7-oxo-4-thia-1-azabicyclo[3.2.0]heptane-2-carboxylic acid; (6R,7R,Z)-7-(2-(2-aminothiazol-4-yl)-2-(2-carboxypropan-2-yloxyimino)acetamido)-8-oxo-3-(pyridinium-1-ylmethyl)-5-thia-1-aza-bicyclo[4.2.0]oct-2-ene-2-carboxylate; (6R,7R,Z)-3-(acetoxymethyl)-7-(2-(2-aminothiazol-4-yl)-2-(methoxyimino)acetamido)-8-oxo-5-thia-1-azabicyclo[4.2.0]oct-2-ene-2-carboxylic acid; (6R,7R)-7-[(2Z)-2-ethoxyimino-2-[5-(phosphonoamino)-1,2,4-thiadiazol-3-yl]acetyl]amino]-3-[4-(1-methylpyridin-1-ium-4-yl)-1,3-thiazol-2-yl]sulfanyl]-8-oxo-5-thia-1-azabicyclo[4.2.0]oct-2-ene-2-carboxylate; (6R,7R,Z)-7-(2-(2-aminothiazol-4-yl)-2-(methoxyimino)acetamido)-3-((1-methylpyrrolidinium-1-yl)methyl)-8-oxo-5-thia-1-aza-bicyclo[4.2.0]oct-2-ene-2-carboxylate; (6R,7R)-3-{[(aminocarbonyl)oxy]methyl}-7-{[(2Z)-2-(2-furyl)-2-(methoxyimino) acetyl]amino}-8-oxo-5-thia-1-azabicyclo[4.2.0]oct-2-ene-2-carboxylic acid; (6R,7R)-7-{[(2Z)-2-(2-amino-1,3-thiazol-4-yl)-2-(methoxyimino)acetyl]amino}-3-{[(2-methyl-5,6-dioxo-1,2,5,6-tetrahydro-1,2,4-triazin-3-yl)thio]methyl}-8-oxo-5-thia-1-azabicyclo[4.2.0]oct-2-ene-2-carboxylic acid; (2S,5R,6R)-6-{[(2R)-2-amino-2-(4-hydroxyphenyl)-acetyl]amino}-3,3-dimethyl-7-oxo-4-thia-1-azabicyclo[3.2.0]heptane-2-carboxylic acid; 3-[5-(dimethylcarbamoyl) pyrrolidin-2-yl]sulfanyl-6-(1-hydroxyethyl)-4-methyl-7-oxo-1-azabicyclo[3.2.0]hept-2-ene-2-carboxylic acid.

In a particular embodiment of the method, the pharmaceutical composition comprises polymorph Ia and (2S,5R,6R)-3,3-dimethyl-7-oxo-6-(2-phenylacetamido)-4-thia-1-zabicyclo[3.2.0]heptane-2-carboxylic acid, or a pharmaceutically acceptable isomer, salt, ester, hydrate, solvate, or combination thereof.

In another particular embodiment of the method, the pharmaceutical composition comprises polymorph Ia and (5R,6S)-6-[(1R)-1-hydroxyethyl]-3-({2-[(iminomethyl)amino]ethyl}thio)-7-oxo-1-azabicyclo[3.2.0]hept-2-ene-2-carboxylic acid, or a pharmaceutically acceptable isomer, salt, ester, hydrate, solvate, or combination thereof.

In another particular embodiment of the method, the pharmaceutical composition comprises polymorph Ia and (5R,6S)-6-((R)-1-hydroxyethyl)-7-oxo-3-((R)-tetrahydrofuran-2-yl)-4-thia-1-azabicyclo[3.2.0]hept-2-ene-2-carboxylic acid, or a pharmaceutically acceptable isomer, salt, ester, hydrate, solvate, or combination thereof.

In another particular embodiment of the method, the pharmaceutical composition comprises polymorph Ia and (2S,5R,6R)-6-{[3-(2-chlorophenyl)-5-methyl-oxazole-4-carbonyl]amino}-3,3-dimethyl-7-oxo-4-thia-1-azabicyclo[3.2.0]heptane-2-carboxylic acid, or a pharmaceutically acceptable isomer, salt, ester, hydrate, solvate, or combination thereof.

In another particular embodiment of the method, the pharmaceutical composition comprises polymorph Ia and (6R,7R,Z)-7-(2-(2-aminothiazol-4-yl)-2-(2-carboxypropan-2-yloxyimino)acetamido)-8-oxo-3-(pyridinium-1-ylmethyl)-5-thia-1-aza-bicyclo[4.2.0]oct-2-ene-2-carboxylate, or a pharmaceutically acceptable isomer, salt, ester, hydrate, solvate, or combination thereof.

In another particular embodiment of the method, the pharmaceutical composition comprises polymorph Ia and (6R,7R,Z)-3-(acetoxymethyl)-7-(2-(2-aminothiazol-4-yl)-2-(methoxyimino)acetamido)-8-oxo-5-thia-1-azabicyclo[4.2.0]oct-2-ene-2-carboxylic acid, or a pharmaceutically acceptable isomer, salt, ester, hydrate, solvate, or combination thereof.

In another particular embodiment of the method, the pharmaceutical composition comprises polymorph Ia and (6R,7R)-7-[(2Z)-2-ethoxyimino-2-[5-(phosphonoamino)-1,2,4-thiadiazol-3-yl]acetyl]amino]-3-[4-(1-methylpyridin-1-ium-4-yl)-1,3-thiazol-2-yl]sulfanyl]-8-oxo-5-thia-1-azabicyclo[4.2.0]oct-2-ene-2-carboxylate, or a pharmaceutically acceptable isomer, salt, ester, hydrate, solvate, or combination thereof.

In another particular embodiment of the method, the pharmaceutical composition comprises polymorph Ia and (6R,7R,Z)-7-(2-(2-aminothiazol-4-yl)-2-(methoxyimino)acetamido)-3-((1-methylpyrrolidinium-1-yl)methyl)-8-oxo-5-thia-1-aza-bicyclo[4.2.0]oct-2-ene-2-carboxylate, or a pharmaceutically acceptable isomer, salt, ester, hydrate, solvate, or combination thereof.

In another particular embodiment of the method, the pharmaceutical composition comprises polymorph Ia and (6R,7R)-3-{[(aminocarbonyl)oxy]methyl}-7-{[(2Z)-2-(2-furyl)-2-(methoxyimino) acetyl]amino}-8-oxo-5-thia-1-azabicyclo[4.2.0]oct-2-ene-2-carboxylic acid, or a pharmaceutically acceptable isomer, salt, ester, hydrate, solvate, or combination thereof.

In another particular embodiment of the method, the pharmaceutical composition comprises polymorph Ia and (6R,7R)-7-{-[(2Z)-2-(2-amino-1,3-thiazol-4-yl)-2-(methoxyimino)acetyl]amino}-3-{[(2-methyl-5,6-dioxo-1,2,5,6-tetrahydro-1,2,4-triazin-3-yl)thio]methyl}-8-oxo-5-thia-1-azabicyclo[4.2.0]oct-2-ene-2-carboxylic acid, or a pharmaceutically acceptable isomer, salt, ester, hydrate, solvate, or combination thereof.

In another particular embodiment of the method, the pharmaceutical composition comprises polymorph Ia and (2S,5R,6R)-6-{[(2R)-2-amino-2-(4-hydroxyphenyl)-acetyl]amino}-3,3-dimethyl-7-oxo-4-thia-1-azabicyclo[3.2.0]heptane-2-carboxylic acid, or a pharmaceutically acceptable isomer, salt, ester, hydrate, solvate, or combination thereof.

In another particular embodiment of the method, the pharmaceutical composition comprises polymorph Ia and 3-[5-(dimethylcarbamoyl) pyrrolidin-2-yl]sulfanyl-6-(1-hydroxyethyl)-4-methyl-7-oxo-1-azabicyclo[3.2.0]hept-2-ene-2-carboxylic acid, or a pharmaceutically acceptable isomer, salt, ester, hydrate, solvate, or combination thereof.

In another particular embodiment of the method, the pharmaceutical composition comprises polymorph Ia and (2S,5R,6R)-6-[(R)-2-(4-ethyl-2,3-dioxo-1-piperazinecarboxamido)-2-phenylacetamido]-3,3-dimethyl-7-oxo-4-thia-1-azabicyclo[3.2.0]heptane-2-carboxylic acid, or a pharmaceutically acceptable isomer, salt, ester, hydrate, solvate, or combination thereof. In another particular embodiment, the bacterial infection is caused by bacteria that are susceptible to the composition comprising polymorph Ia and (2S,5R,6R)-6-[(R)-2-(4-ethyl-2,3-dioxo-1-piperazinecarboxamido)-2-phenylacetamido]-3,3-dimethyl-7-oxo-4-thia-1-azabicyclo[3.2.0]heptane-2-carboxylic acid, or a pharmaceutically acceptable isomer, salt, ester, hydrate, solvate, or combination thereof.

In another aspect, provided herein is a method for the treatment of bacterial infections in a mammal, comprising administering to said mammal a therapeutically effective amount of a pharmaceutical composition comprising an antibiotic and a crystalline tazobactam arginine compound (e.g., of the polymorph Ia solid form). The crystalline tazobactam arginine can be characterized by an X-ray powder diffraction pattern having peaks expressed in degrees 2-Theta at angles of 4.8°±0.3°, 8.9°±0.3°, 11.3°±0.3°, 14.9°±0.3°, 18.0°±0.3°, 19.4°±0.3°, 21.3°±0.3°, 22.8°±0.3° and 24.3°±0.3°.

Non-limiting examples of bacterial infections that can be treated by the methods of the invention include infections caused by: aerobic and facultative gram-positive microorganisms (e.g., *Staphylococcus aureus*, *Enterococcus faecalis*, *Staphylococcus epidermidis*, *Streptococcus agalactiae*, *Streptococcus pneumonia*, *Streptococcus pyogenes*, *Viridans group streptococci*), aerobic and facultative gram-negative microorganisms (e.g., *Acinetobacter baumanii*, *Escherichia coli*, *Haemophilus influenza*, *Klebsiella pneumonia*, *Pseudomonas aeruginosa*, *Citrobacter koseri*, *Moraxella catarrhalis*, *Morganella morganii*, *Neisseria gonorrhoeae*, *Proteus mirabilis*, *Proteus vulgaris*, *Serratia marcescens*, *Providencia stuartii*, *Providencia rettgeri*, *Salmonella enterica*), gram-positive anaerobes (*Clostridium perfringens*), and gram-negative anaerobes (e.g., *Bacteroides fragilis* group (e.g., *B. fragilis*, *B. ovatus*, *B. thetaiotaomicron*, and *B. vulgates*), *Bacteroides distasonis*, *Prevotella melaminogenica*).

In certain embodiments of the methods described herein, bacterial infection resulting from beta-lactamase-producing organisms are treated or controlled. Non-limiting examples of beta-lactamase-producing organisms include:

(1) ESBL (extended-spectrum beta-lactamase)-producing organisms selected from the group consisting of *Enterobacteriaceae* spp.: *Escherichia coli*, *Klebsiella* spp. (including *K. pneumoniae* and *K. oxytoca*), *Proteus mirabilis*, *Proteus vulgaris*, *Enterobacter* spp., *Serratia* spp., *Citrobacter* spp., *Pseudomonas* spp., *Acinetobacter* spp.) and *Bacteroides* spp.;

(2) CSBL (conventional-spectrum beta-lactamase)-producing organisms, known to those of skill in the art; and (3) Inducible-AmpC-type beta-lactamases, such as *Citrobacter* spp., *Serratia* spp., *Morganella morganii*, *Proteus vulgaris*, and *Enterobacter cloacae*.

In certain embodiments of the methods described herein, bacterial infection is associated with one or more of the following conditions:

Appendicitis (complicated by rupture or abscess) and peritonitis caused by piperacillin-resistant beta-lactamase producing strains of *Escherichia coli* or the following members of the *Bacteroides fragilis* group: *B. fragilis*, *B. ovatus*, *B. thetaiotaomicron*, or *B. vulgates*;

Uncomplicated and complicated skin and skin structure infections, including cellulitis, cutaneous abscesses, and ischemic/diabetic foot infections caused by piperacillin-resistant, beta-lactamase producing strains of *Staphylococcus aureus*;

Postpartum endometritis or pelvic inflammatory disease caused by piperacillin-resistant, beta-lactamase producing strains of *Escherichia coli*;

Community-acquired pneumonia (moderate severity only) caused by piperacillin-resistant, beta-lactamase producing strains of *Haemophilus influenza*;

Nosocomial pneumonia (moderate to severe) caused by piperacillin-resistant, beta-lactamase producing strains of *Staphylococcus aureus* and by *Acinetobacter baumanii*, *Haemophilus influenzae*, *Klebsiella pneumoniae*, and *Pseudomonas aeruginosa*.

Complicated intra-abdominal infections; Complicated urinary tract infections (cUTIs); Acute Pyelonephritis; Systemic Inflammatory Response Syndrome (SIRS).

Also provided herein is the use of a crystalline tazobactam arginine, and hydrates and solvates thereof, in combination with one or more beta-lactam compounds, for the manufacture of a medicament for the treatment of bacterial infection. The bacterial infection can result from either gram-negative or gram-positive organisms. In one embodiment, the crystalline tazobactam arginine is polymorph Ia. Polymorph Ia is characterized as described above. Said one or more beta-lactam compounds can be selected from the group consisting of penicillins, cephalosporins, carbapenems, and combinations thereof. In certain embodiments, said one or more beta-lactam compounds are selected from the compounds listed in Table 2, and pharmaceutically acceptable isomers, salts, esters, hydrates, solvates, or combinations thereof.

Also provided herein is tazobactam arginine, and hydrates and solvates thereof, for use in a method of treating bacterial infection. In some embodiments, a combination of tazobactam arginine and one or more beta-lactam compounds is used in said method.

As used herein, "treating", "treat" or "treatment" describes the management and care of a patient for the purpose of combating a disease, condition, or disorder and includes the administration of a pharmaceutical composition of the present invention to alleviate the symptoms or complications of a disease, condition or disorder, or to eliminate the disease, condition or disorder. The term "treat" can also include treatment of a cell in vitro or an animal model.

By a "therapeutically effective amount" of a compound of the invention is meant a sufficient amount of the compound to treat the disorder (e.g., bacterial infection). The specific therapeutically effective amount that is required for the treatment of any particular patient or organism (e.g., a mammal) will depend upon a variety of factors including the disorder being treated and the severity of the disorder; the activity of the specific compound or composition employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety). The therapeutically effective amount for a given situation can be readily determined by routine experimentation and is within the skill and judgment of the ordinary clinician.

Assays

Provided herein is a method for detecting or identifying an agent that will inhibit one or more beta-lactamase-producing organisms, said method comprising combining:
(a) a test agent;
(b) a composition comprising one or more beta-lactamase-producing organisms; and
(c) a beta-lactamase inhibitor; and
detecting or measuring a change in the activity of the beta-lactamase-producing organisms, wherein a decrease in the acitivity of the beta-lactamase-producing organisms indicates that the test agent inhibits the beta-lactamase-producing organisms.

As used in the above method, "activity" refers to the ability of the beta-lactamase-producing organism to reproduce and/or infect another organism, or "activity" refers to the presence of an indicator of the ability of the beta-lactamase-producing organism to reproduce and/or infect another organism. Methods for detecting and/or measuring changes in the activity of beta-lactamase-producing organisms are known to those of skill in the art.

In another aspect, provided herein is a method of determining the susceptibility of a beta-lactamase-producing organism to a composition comprising a beta-lactam compound and a beta-lactamase inhibitor. The in vitro activity of compositions of the subject invention may be assessed by standard testing procedures. Non-limiting examples of such a procedure include the Kirby-Bauer method, the Stokes test, the E-test, broth dilution and agar dilution for determination of minimum inhibitory concentration (MIC), as described in "Approved Standard. Methods for Dilution Antimicrobial Susceptibility Tests for Bacteria that Grow Aerobically," 3.sup.rd ed., published 1993 by the National Committee for Clinical Laboratory standards, Villanova, Pa., USA. In certain embodiments, the methods described herein are performed using automation (e.g., Siemens' MicroScan Systems).

In one embodiment of the above methods, the beta-lactamase inhibitor is tazobactam arginine. In a preferred embodiment, the beta-lactamase inhibitor is tazobactam arginine polymorph Ia.

The test agent can be selected from the group consisting of penicillins, cephalosporins, carbapenems, and combinations thereof. In some embodiments, the test agent is selected from the compounds listed in Table 2, and pharmaceutically acceptable isomers, salts, esters, hydrates, solvates, or combinations thereof.

In certain embodiments of the methods described herein, beta-lactamase-producing organisms are selected from the group comprising:

(1) ESBL (extended-spectrum beta-lactamase)-producing organisms selected from the group consisting of *Enterobacteriaceae* spp.: *Escherichia coli, Klebsiella* spp. (including *K. pneumoniae* and *K. oxytoca*), *Proteus mirabilis, Proteus vulgaris, Enterobacter* spp., *Serratia* spp., *Citrobacter* spp.) and *Bacteroides* spp.;

(2) CSBL (conventional-spectrum beta-lactamase)-producing organisms, known to those of skill in the art; and (3) Inducible-AmpC-type beta-lactamases, such as *Citrobacter* spp., *Serratia* spp., *Morganella morganii, Proteus vulgaris*, and *Enterobacter cloacae*.

EXAMPLES

Example 1

Preparation of Tazobactam Arginine Amorphous

Figure 5:
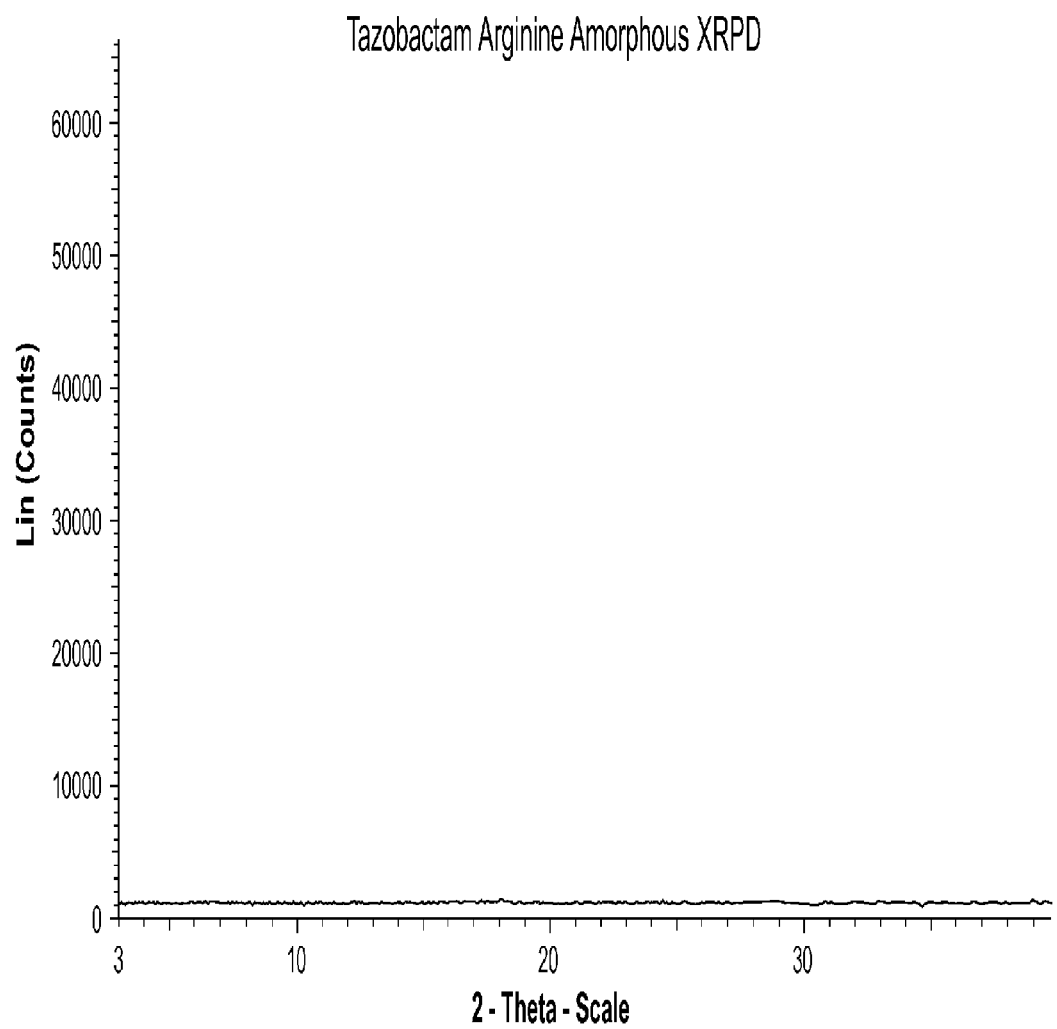
FIG. 5 depicts the X-ray powder diffraction pattern of tazobactam arginine amorphous.

L-arginine (2.9 g) was dissolved in 100 mL of deionized water and 5.0 g of tazobactam acid was then added, resulting a homogenous solution. The solution was lyophilized overnight to yield tazobactam arginine amorphous as an off-white solid (8.0 g). The XRPD spectrum of the tazobactam arginine amorphous is depicted in FIG. 5.

Example 2

Preparation of Tazobactam Arginine Crystalline Polymorph Ia

Tazobactam arginine amorphous (1.00 g) was dissolved in 10.0 mL of deionized water. 30 mL of acetone was added to the aqueous solution by drop-wise addition. The mixture was allowed to sit overnight at ambient temperature, resulting in white fine needles. After filtration and vacuum drying for 4 hours, tazobactam arginine polymorph Ia (516 mg) was obtained. The XRPD spectrum of the tazobactam arginine polymorph Ia is depicted in FIG. 1.

Example 3

Preparation of Tazobactam Arginine Crystalline Polymorph Ia

L-arginine (1.16 g) was charged to the reactor and dissolved in a mixture of deionized water-acetone (1:1, v/v, 40 mL) by mechanically stirring at 300 rpm, 30° C. over 5 min. Tazobactam acid (2.00 g) was then added to the above solution over 2 min with the observed pH change from 10.5±0.5 to 5.9±0.5. After adding 34.5 mL of acetone over 30 min at 30° C., crystallization started, then the suspension was cooled down to 15° C. at 0.1° C./min and kept stirring at 15° C. for additional 1.5 hr. White fine needle crystals were filtered out and vacuum dried for 2 hours at 35° C. to obtain 2.59 g (82% yield) of tazobactam arginine polymorph Ia.

Example 4

Figure 6:
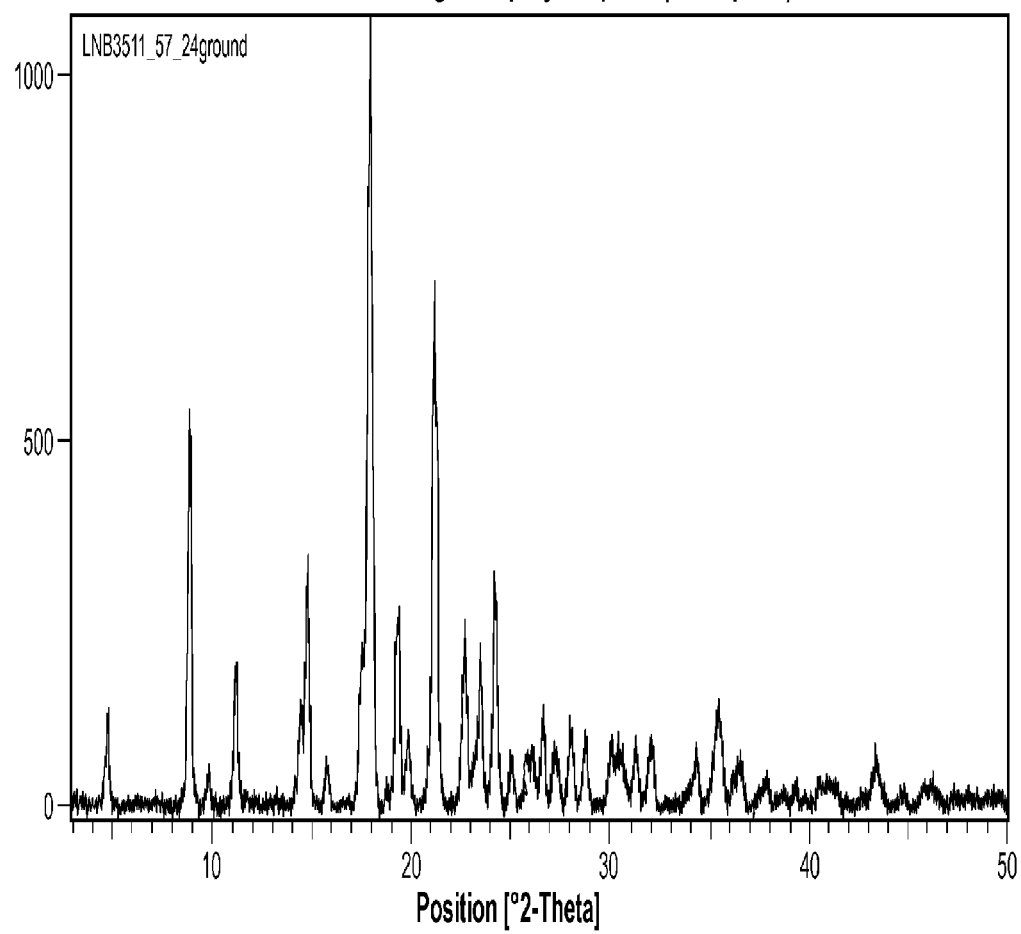
FIG. 6 depicts the X-ray power diffraction pattern of polymorph Ia (Example 4).

Preparation of Tazobactam Arginine Crystalline Polymorph Ia-20 g Scale 1) 20 g of tazobactam acid and 1 equivalent of L-arginine was placed into a jacketed, glass, 1 liter laboratory reactor with an overhead stirrer.
2) 5 volumes (relative to tazobactam acid weight) of ambient temperature (ca. 22° C.) water was added to the reactor and stirred at 480 rpm. The reactor temperature was maintained between 23-27° C. with a target temperature of 25° C. The reaction was stirred for 10-15 minutes in order to obtain complete dissolution. Stirring at 480 rpm was maintained throughout the reaction.
3) 0.75 vol. ambient temperature deionised water was added to the reactor. This step was included to account for the sterile filtration and washing step required in the process.
4) 8 volumes (160 ml) of acetone was added over 10 minutes.
5) The reaction mixture was aged for 15 minutes, at which point precipitation of tazobactam arginine begins.
6) A controlled cool was started from 25° C. down to 10° C. over 1.5 hours at a rate of 10° C./hour.
7) After reaching 10° C., 18 volumes of acetone was added over two hours (i.e., total acetone added throughout reaction was 26 volumes).
8) After the acetone addition, the reaction mixture was allowed to age for 1 hour.
9) The reaction mixture was filtered and washed with 5 volumes of cold acetone (ca. 4° C.).
10) The resulting solid was dried at ambient (ca. 22° C.) under vacuum and nitrogen bleed for 24 hours with regular mixing of the solid, to furnish polymorph Ia in 90% yield. The XRPD spectrum of the tazobactam arginine polymorph Ia is depicted in FIG. 6.

Figure 7:
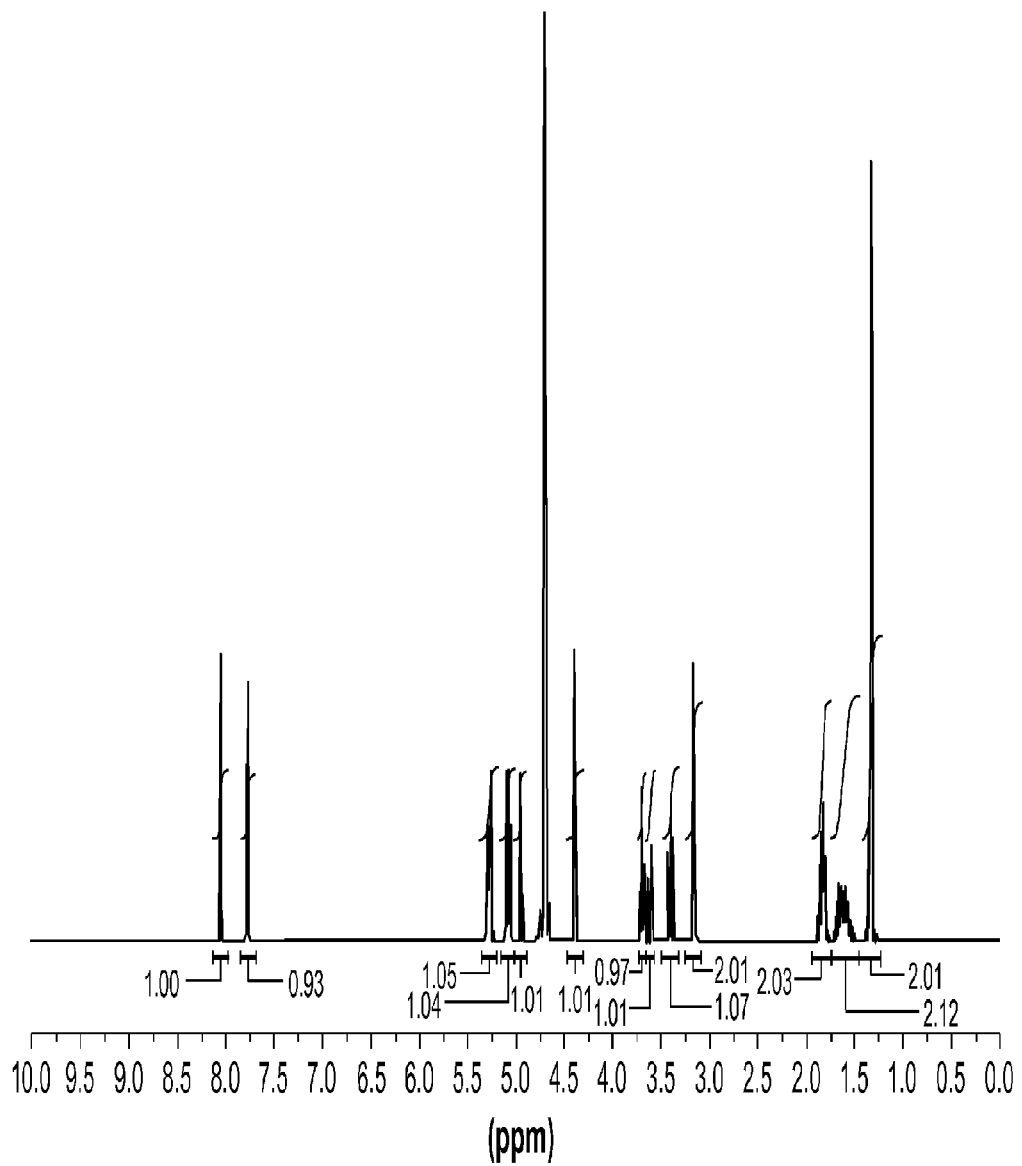
FIG. 7 depicts the $^1$H-NMR spectrum of polymorph Ia.

The $^1$H-NMR spectrum (FIG. 7) of polymorph Ia indicates a stoichiometry of 1:1 tazobactam acid:arginine.

Example 5

Preparation of Tazobactam Arginine Polymorph Ia—Isopropanol Antisolvent 1) 20 g of tazobactam acid and 1 equivalent of L-arginine was placed into a 1 liter reactor.
2) 5 volumes (ca. 100 ml) of water (relative to tazobactam acid weight) was added to the reactor and stirred at 300 rpm (25° C.) for 10-15 minutes in order to obtain complete dissolution.
3) A further 0.75 vol water was then added to account for washing in sterile filtration step.
4) 6 volumes (120 ml) of ispopropanol was added over ca. 15 minutes in order to initiate precipitation.
5) The suspension was then aged for 15 minutes before cooling down to 10° C. over 1.5 hours at a rate of 10° C./hour.
6) After reaching 10° C., isopropanol addition was started at a rate of 185 ml/hour, adding a further 16 volumes (i.e., total isopropanol added throughout reaction was 24 volumes).
7) The reaction was then allowed to age for 1 hour.
8) The suspension was then filtered and washed with 5 volumes of cold isopropanol (ca. 4° C.).
9) The resulting solid was then dried at ambient under vacuum and nitrogen bleed for 24 hours with regular mixing of the solids to yield tazobactam arginine crystalline polymorph Ia.

Example 6

Hygroscopicity Experiments

Analysis by DVS was performed on a VTI SGA-100 water vapor sorption analyser using approximately 18-23 mg of each sample. Each sample was pre-dried at 60° C. for a maximum of 1 hour and then analyzed at 25° C. in 10% relative humidity (RH) steps from 5-95% (adsorption) and then 90-10% RH (desorption). The sample was equilibrated to each humidity level for a maximum of 3 hours or until constant weight was attained. Equilibrium criteria were set at less than 0.0050% weight change within 5 minutes.

Figure 8:
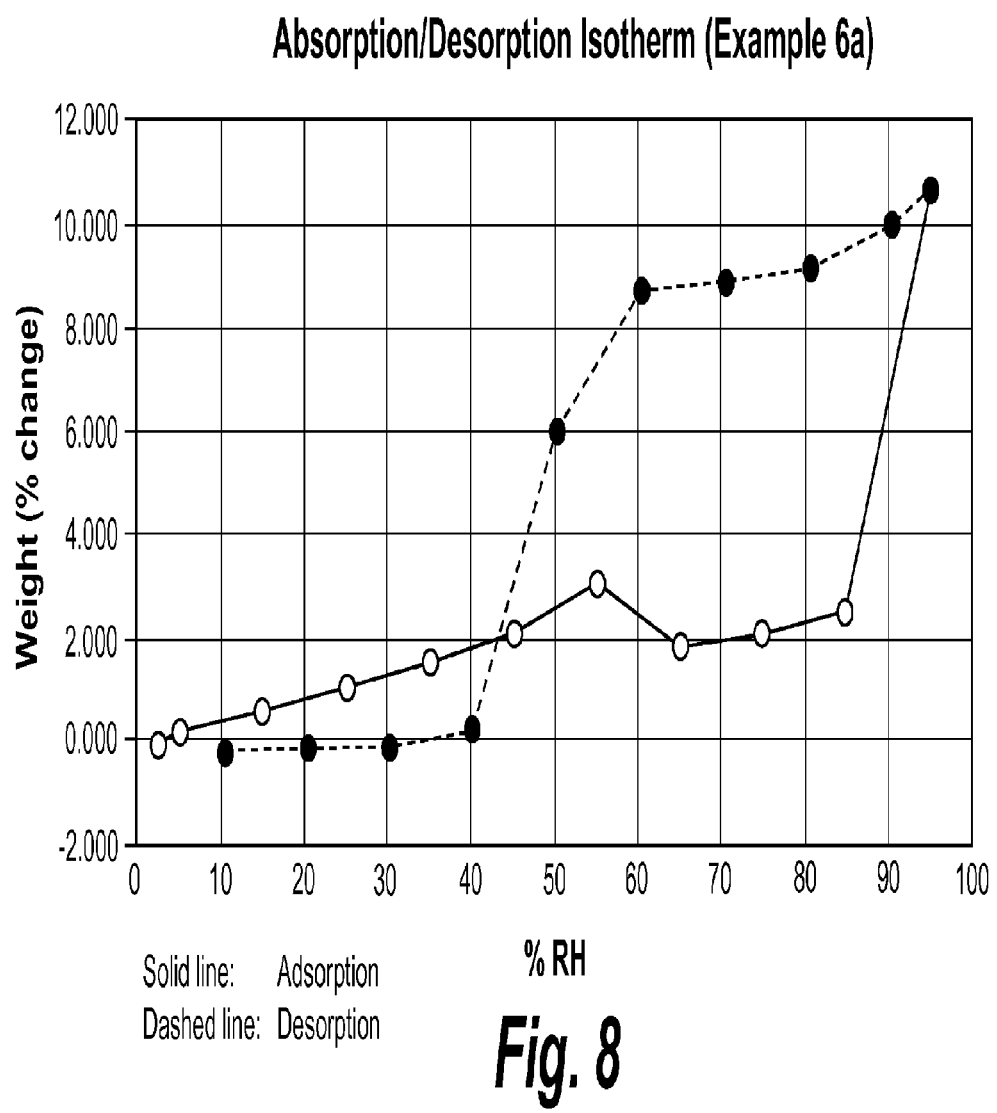
FIG. 8 depicts the DVS graph of tazobactam arginine amorphous (Example 6a).

(6a) Tazobactam arginine amorphous exhibited approximately 10.7% weight increase at 95% relative humidity (RH). See FIG. 8.

Figure 9:
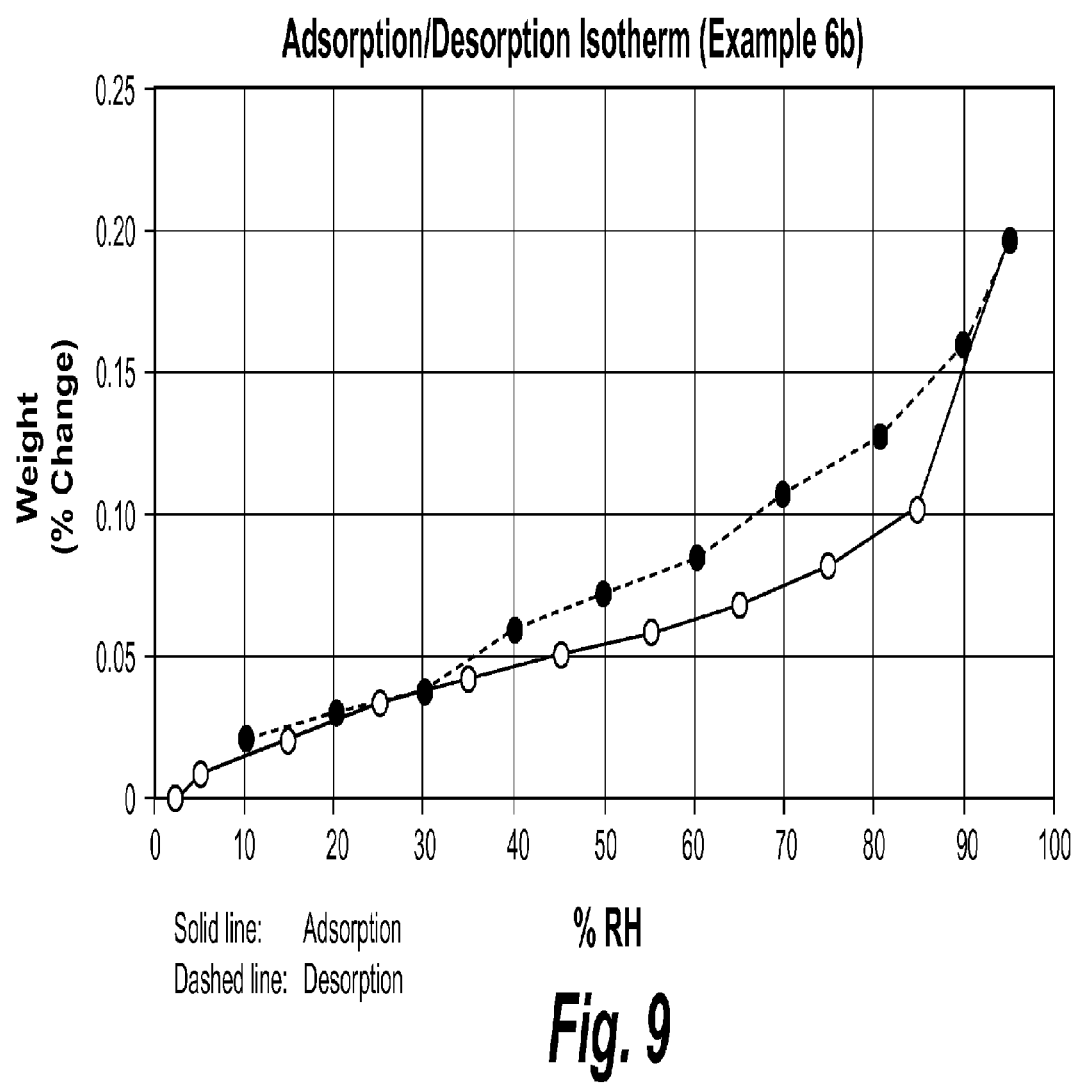
FIG. 9 depicts the DVS graph of polymorph Ia (Example 6b).

(6b) Tazobactam arginine polymorph Ia exhibited approximately 0.2% weight increase at 95% RH. See FIG. 9.

Figure 10:
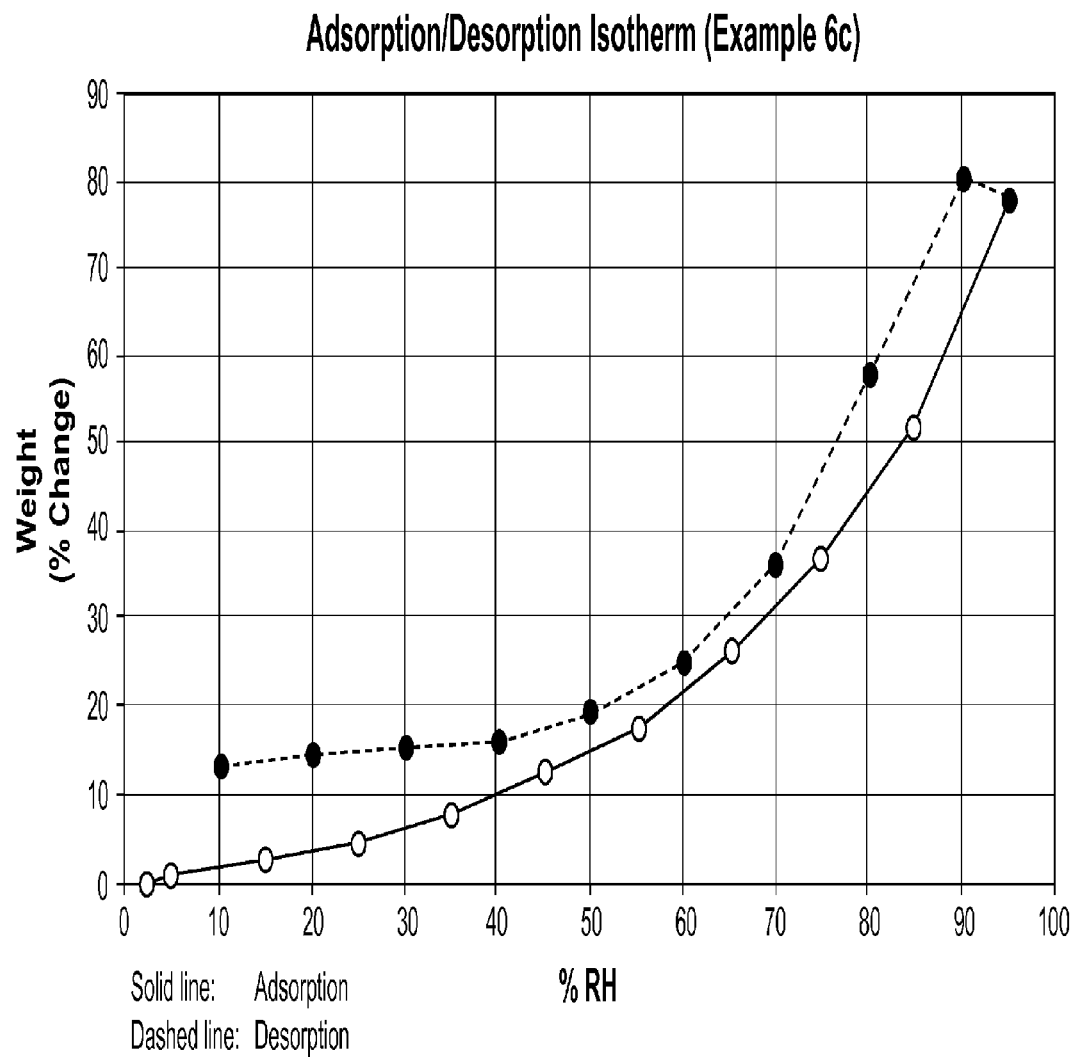
FIG. 10 depicts the DVS graph of amorphous tazobactam sodium (Example 6c).

(6c) Amorphous tazobactam sodium exhibited approximately 80% weight increase at 95% RH. See FIG. 10.

Example 7

Solvent Solubility Screen

The solvent solubility screen was carried out using a solvent addition technique. For each of 25 solvent systems, the following procedure was used: (1) about 20 mg of crystalline tazobactam arginine was placed into a vial; (2) solvent was added to the vial in 5 volume aliquots (100 µL) until complete dissolution, or 100 volumes, had been added; (3) between additions, the sample was heated to about 50° C. in order to determine the approximate solubility at an elevated temperature; (4) if 100 volumes was reached and complete dissolution was not observed, solubility was calculated to be below that point. Results of the solvent solubility screen are shown in Table 3.

Instrumentation and Methods

I. X-Ray Powder Diffraction (XRPD) experiments were performed using a Bruker D8 Advance X-ray powder diffractometer utilizing a zero return silicon plate. A suitable amount of sample was placed directly on the sample holder, pressed flat to smooth, and analyzed from 3°-40° 2θ using Bragg-Brentano optics. A step size of 0.01° and a step time of 0.3 sec/step were utilized. Analysis was started immediately following sample preparation.

II. Differential Scanning calorimetry (DSC) experiments were performed on a TA Instruments Q100 instrument. A temperature range of 40° C. to 300° C. with a ramp rate of 10° C./minute was utilized. Approximately 1.0 mg of sample was weighed into a tared aluminum sample pan and sealed hermetically. A small hole was pushed into the cover of the sample pan to allow for pressure release.

III. Thermo Gravimetric Analysis (TGA) experiments were performed on a TA Instruments 5000 instrument from 20 to 300° C. with a heating rate of 10° C./minute for all samples.

Tables

TABLE 1

XRPD Scanning Data of Tazobactam Arginine Polymorph Ia (FIG. 1)

| Chord Mid. 2-Theta° | D (Obs. Angstrom | Intensity % % | Max Int. Cps | Intensity Count | I. Breadth 2-Theta° |
|---|---|---|---|---|---|
| 4.818 | 18.27951 | 33.5 | 130 | 7043 | 0.166 |
| 8.978 | 9.83463 | 100.0 | 364 | 21035 | 0.174 |

TABLE 1-continued

XRPD Scanning Data of Tazobactam Arginine Polymorph Ia (FIG. 1)

| Chord Mid. 2-Theta° | D (Obs. Angstrom) | Intensity % | Max Int. Cps | Intensity Count | I. Breadth 2-Theta° |
|---|---|---|---|---|---|
| 9.916 | 8.90757 | 8.7 | 32.3 | 1832 | 0.168 |
| 11.301 | 7.81865 | 27.8 | 104 | 5844 | 0.167 |
| 14.521 | 6.09321 | 20.2 | 75.5 | 4251 | 0.108 |
| 14.902 | 5.93864 | 27.8 | 102 | 5850 | 0.162 |
| 15.93 | 5.56039 | 1.9 | 7.2 | 394 | 0.148 |
| 16.947 | 5.23254 | 1.2 | 4.96 | 253 | 0.169 |
| 17.581 | 5.04332 | 6.8 | 24.8 | 1429 | 0.182 |
| 18.046 | 4.91261 | 48.7 | 184 | 10242 | 0.189 |
| 18.863 | 4.70152 | 2.6 | 9.41 | 545 | 0.159 |
| 19.418 | 4.5672 | 31.6 | 115 | 6637 | 0.166 |
| 19.943 | 4.44853 | 9.3 | 33.8 | 1966 | 0.181 |
| 21.31 | 4.1658 | 41.4 | 151 | 8714 | 0.192 |
| 22.797 | 3.89704 | 9.1 | 33.2 | 1921 | 0.201 |
| 23.587 | 3.76939 | 14.7 | 53.1 | 3082 | 0.171 |
| 24.345 | 3.65381 | 19.6 | 71.2 | 4116 | 0.208 |
| 25.169 | 3.53603 | 2.3 | 8.44 | 479 | 0.185 |
| 25.895 | 3.43955 | 5.4 | 19.7 | 1129 | 0.152 |
| 26.221 | 3.39654 | 5.0 | 15.6 | 1061 | 0.146 |
| 26.689 | 3.33736 | 11.1 | 40 | 2329 | 0.192 |
| 27.249 | 3.27088 | 5.0 | 19.1 | 1052 | 0.25 |
| 28.09 | 3.17445 | 5.6 | 20.2 | 1184 | 0.269 |
| 28.886 | 3.08881 | 3.2 | 11.4 | 666 | 0.219 |
| 30.129 | 2.96435 | 4.2 | 15.6 | 884 | 0.184 |
| 30.585 | 2.92187 | 1.8 | 6.17 | 369 | 0.313 |
| 31.413 | 2.84617 | 5.6 | 20.1 | 1174 | 0.212 |
| 32.162 | 2.78029 | 2.8 | 9.87 | 583 | 0.285 |
| 33.878 | 2.64293 | 1.1 | 2.36 | 236 | 0.109 |
| 34.419 | 2.60386 | 3.2 | 11.5 | 676 | 0.239 |
| 35.529 | 2.52408 | 6.0 | 21.9 | 1254 | 0.344 |
| 36.598 | 2.45267 | 3.0 | 11 | 621 | 0.269 |
| 37.924 | 2.37119 | 1.8 | 6.41 | 371 | 0.276 |
| 38.818 | 2.31643 | 1.4 | 2.74 | 295 | 0.172 |
| 39.398 | 2.28753 | 1.1 | 3.56 | 236 | 0.196 |

TABLE 2

Beta-lactam compounds

| No. | IUPAC Name | CAS No. |
|---|---|---|
| 1 | (2S,5R,6R)-6-[(R)-2-(4-ethyl-2,3-dioxo-1-piperazinecarboxamido)-2-phenylacetamido]-3,3-dimethyl-7-oxo-4-thia-1-azabicyclo[3.2.0]heptane-2-carboxylic acid | 61477-96-1 |
| 2 | (2S,5R,6R)-3,3-dimethyl-7-oxo-6-(2-phenylacetamido)-4-thia-1-zabicyclo[3.2.0]heptane-2-carboxylic acid | 61-33-6 |
| 3 | (5R,6S)-6-[(1R)-1-hydroxyethyl]-3-({2-[(iminomethyl)amino]ethyl}thio)-7-oxo-1-azabicyclo[3.2.0]hept-2-ene-2-carboxylic acid | 74431-23-5 |
| 4 | (5R,6S)-6-((R)-1-hydroxyethyl)-7-oxo-3((R)-tetrahydrofuran-2-yl)-4-thia-1-azabicyclo[3.2.0]hept-2-ene-2-carboxylic acid faropenem | 106560-14-9 |
| 5 | (2S,5R,6R)-6-{[3-(2-chlorophenyl)-5-methyl-oxazole-4-carbonyl]amino}-3,3-dimethyl-7-oxo-4-thia-1-azabicyclo[3.2.0]heptane-2-carboxylic acid | 61-72-3 |
| 6 | (6R,7R,Z)-7-(2-(2-aminothiazol-4-yl)-2-(2-carboxypropan-2-yloxyimino)acetamido)-8-oxo-3-(pyridinium-1-ylmethyl)-5-thia-1-azabicyclo[4.2.0]oct-2-ene-2-carboxylate | 72558-82-8 |
| 7 | (6R,7R,Z)-3-(acetoxymethyl)-7-(2-(2-aminothiazol-4-yl)-2-(methoxyimino)acetamido)-8-oxo-5-thia-1-azabicyclo[4.2.0]oct-2-ene-2-carboxylic acid | 63527-52-6 |
| 8 | (6R,7R)-7-[(2Z)-2-ethoxyimino-2-[5-(phosphonoamino)-1,2,4-thiadiazol-3-yl]acetyl]amino]-3-[4-(1-methylpyridin-1-ium-4-yl)-1,3-thiazol-2-yl]sulfanyl]-8-oxo-5-thia-1-azabicyclo[4.2.0]oct-2-ene-2-carboxylate | 400827-46-5 |
| 9 | (6R,7R,Z)-7-(2-(2-aminothiazol-4-yl)-2-(methoxyimino)acetamido)-3-((1-methylpyrrolidinium-1-yl)methyl)-8-oxo-5-thia-1-azabicyclo[4.2.0]oct-2-ene-2-carboxylate | 88040-23-7 |
| 10 | (6R,7R)-3-{(aminocarbonyl)oxy]methyl}-7-{(2Z)-2-(2-furyl)-2-(methoxyimino) acetyl]amino}-8-oxo-5-thia-1-azabicyclo[4.2.0]oct-2-ene-2-carboxylic acid | 55268-75-2 |
| 11 | (6R,7R)-7-1{[(2Z)-2-(2-amino-1,3-thiazol-4-yl)-2-(methoxyimino)acetyl]amino}-3-{[(2-methyl-5,6-dioxo-1,2,5,6-tetrahydro-1,2,4-triazin-3-yl)thio]methyl}-8-oxo-5-thia-1-azabicyclo[4.2.0]oct-2-ene-2-carboxylic acid | 73384-59-5 |
| 12 | (2S,5R,6R)-6-{(2R)-2-amino-2-(4-hydroxyphenyl)-acetyl]amino}-3,3-dimethyl-7-oxo-4-thia-1-azabicyclo[3.2.0]heptane-2-carboxylic acid | 26787-78-0 |
| 13 | 3-[5-(dimethylcarbamoyl) pyrrolidin-2-yl] sulfanyl-6-(1-hydroxyethyl)-4-methyl-7-oxo-1-azabicyclo[3.2.0]hept-2-ene-2-carboxylic acid | 119478-56-7 |

TABLE 3

Solvent solubility screen results

| Solvent | Solubility @ 22° C. (mg/ml) | Solubility @ 50° C. (mg/ml) |
|---|---|---|
| Acetic acid | >100 mg/ml | >200 mg/ml |
| Acetone | <10 mg/ml | <10 mg/ml |
| Acetonitrile | <10 mg/ml | <10 mg/ml |
| 1-butanol | <10 mg/ml | <10 mg/ml |
| Cyclohexane | <10 mg/ml | <10 mg/ml |
| Dichloromethane | <10 mg/ml | <10 mg/ml |
| Diisopropyl ether | <10 mg/ml | <10 mg/ml |
| Dimethylformamide | <10 mg/ml | <10 mg/ml |
| Dimethylsulfoxide | <10 mg/ml | ca.10 mg/ml |

TABLE 3-continued

Solvent solubility screen results

| Solvent | Solubility @ 22° C. (mg/ml) | Solubility @ 50° C. (mg/ml) |
|---|---|---|
| 1,4-Dioxane | <10 mg/ml | <10 mg/ml |
| Ethanol | <10 mg/ml | <10 mg/ml |
| Ethyl acetate | <10 mg/ml | <10 mg/ml |
| Heptane | <10 mg/ml | <10 mg/ml |
| Methanol | <10 mg/ml | <10 mg/ml |
| Isopropyl acetate | <10 mg/ml | <10 mg/ml |
| Methyl acetate | <10 mg/ml | <10 mg/ml |
| Methylethyl ketone | <10 mg/ml | <10 mg/ml |
| Methyl isobutyl ketone | <10 mg/ml | <10 mg/ml |
| N-Methyl-2-pyrrolidone | <10 mg/ml | <10 mg/ml |
| Nitromethane | <10 mg/ml | <10 mg/ml |
| 2-Propanol | <10 mg/ml | <10 mg/ml |
| tert-Butylmethyl ether | <10 mg/ml | <10 mg/ml |
| Tetrahydrofuran | <10 mg/ml | <10 mg/ml |
| Toluene | <10 mg/ml | <10 mg/ml |
| Water | >100 mg/ml | >200 mg/ml |

The invention claimed is:

1. A method for the treatment of bacterial infections in a mammal, comprising administering to said mammal a therapeutically effective amount of a pharmaceutical composition comprising tazobactam arginine polymorph Ia.

2. The method of claim 1 wherein the mammal is human.

3. A method for the treatment of bacterial infections in a mammal, comprising administering to said mammal a therapeutically effective amount of a pharmaceutical composition comprising a beta-lactam compound and tazobactam arginine polymorph Ia.

4. The method of claim 3 wherein the mammal is a human.

5. A pharmaceutical composition comprising tazobactam arginine polymorph Ia and one or more beta-lactam compounds, and a pharmaceutically acceptable carrier or diluent.

6. A pharmaceutical composition prepared by a method comprising the step of combining tazobactam arginine polymorph Ia and a beta-lactam compound.

* * * * *